(12) United States Patent
Moseley et al.

(10) Patent No.: US 10,973,949 B2
(45) Date of Patent: *Apr. 13, 2021

(54) MULTIPHASIC BONE GRAFT SUBSTITUTE MATERIAL

(71) Applicant: Agnovos Healthcare, LLC, Rockville, MD (US)

(72) Inventors: Jon P. Moseley, Alrington, TN (US); Jamie MacDougall, Oakland, TN (US); Katie Harrigan, Cordova, TN (US)

(73) Assignee: Agnovos Healthcare, LLC, Rockville, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/238,130

(22) Filed: Aug. 16, 2016

(65) Prior Publication Data

US 2016/0354514 A1 Dec. 8, 2016

Related U.S. Application Data

(63) Continuation of application No. 14/568,773, filed on Dec. 12, 2014, now Pat. No. 9,446,170.

(60) Provisional application No. 62/031,635, filed on Jul. 31, 2014, provisional application No. 61/915,837, filed on Dec. 13, 2013.

(51) Int. Cl.
| | |
|---|---|
| *A61L 27/12* | (2006.01) |
| *C04B 28/34* | (2006.01) |
| *A61L 24/02* | (2006.01) |
| *A61L 27/02* | (2006.01) |
| *A61L 27/36* | (2006.01) |
| *A61L 27/54* | (2006.01) |
| *A61L 27/56* | (2006.01) |
| *A61L 27/58* | (2006.01) |
| *A61L 24/00* | (2006.01) |
| *C04B 28/14* | (2006.01) |
| *A61L 27/38* | (2006.01) |
| *C04B 111/00* | (2006.01) |

(52) U.S. Cl.
CPC .......... *A61L 27/12* (2013.01); *A61L 24/0015* (2013.01); *A61L 24/02* (2013.01); *A61L 27/025* (2013.01); *A61L 27/3608* (2013.01); *A61L 27/3641* (2013.01); *A61L 27/3821* (2013.01); *A61L 27/3847* (2013.01); *A61L 27/54* (2013.01); *A61L 27/56* (2013.01); *A61L 27/58* (2013.01); *C04B 28/14* (2013.01); *C04B 28/34* (2013.01); *A61L 2300/10* (2013.01); *A61L 2300/102* (2013.01); *A61L 2300/112* (2013.01); *A61L 2300/414* (2013.01); *A61L 2400/06* (2013.01); *A61L 2430/02* (2013.01); *C04B 2111/00836* (2013.01)

(58) Field of Classification Search
None
See application file for complete search history.

(56) References Cited

U.S. PATENT DOCUMENTS

| | | |
|---|---|---|
| 2,616,789 A | 11/1952 | Hoggatt |
| 3,197,071 A | 7/1965 | Kuster |
| 3,573,947 A | 4/1971 | Kinkade et al. |
| 3,813,312 A | 5/1974 | Kinkade et al. |
| 4,224,072 A | 9/1980 | Stewart |
| 4,349,518 A | 9/1982 | Long et al. |
| 4,365,356 A | 12/1982 | Broemer et al. |
| 4,371,484 A | 2/1983 | Innkai et al. |
| 4,376,168 A | 3/1983 | Takami et al. |
| 4,595,713 A | 6/1986 | St. John |
| 4,599,085 A | 7/1986 | Riess et al. |
| 4,612,053 A | 9/1986 | Brown et al. |
| 4,619,655 A | 10/1986 | Hanker et al. |
| 4,626,392 A | 12/1986 | Kondo et al. |
| 4,659,617 A | 4/1987 | Fujii et al. |
| 4,673,355 A | 6/1987 | Farris et al. |
| 4,820,306 A | 4/1989 | Gorman et al. |
| 4,838,922 A | 6/1989 | Green |
| 4,843,112 A | 6/1989 | Gerhart et al. |
| 4,861,733 A | 8/1989 | White |
| 4,882,149 A | 11/1989 | Spector |

(Continued)

FOREIGN PATENT DOCUMENTS

| | | |
|---|---|---|
| CN | 101020085 A | 8/2007 |
| CN | 101596330 B | 12/2009 |

(Continued)

OTHER PUBLICATIONS

BIOSORB Resorbable Void Filler (2003).*
International Search Report and Written Opinion for Application No. PCT/US2014/069963, dated Mar. 10, 2015.
International Preliminary Report on Patentability for Application No. PCT/US2014/069963, dated Dec. 2, 2015.
Barralet, et al., "Modification of Calcium Phosphate Cement with a-Hdroxy Acids and Their Salts," Chem. Mater. 2005, vol. 17, pp. 1313-1319.
Bohner et al., "Injectability of Calcium Phosphate Pastes," Biomaterials, 2005, vol. 26, pp. 1553-1563.

(Continued)

*Primary Examiner* — Celeste A Roney
(74) *Attorney, Agent, or Firm* — Wolf, Greenfield & Sacks, P.C.

(57) ABSTRACT

The invention provides a particulate composition adapted for forming a bone graft substitute cement upon mixing with an aqueous solution, comprising i) a calcium sulfate hemihydrate powder, wherein the calcium sulfate hemihydrate is present at a concentration of at least about 50 weight percent based on the total weight of the particulate composition; ii) a monocalcium phosphate monohydrate powder; iii) a nonporous β-tricalcium phosphate powder; and iv) a porous β-tricalcium phosphate powder. Bone graft substitute cements made therefrom, a bone graft substitute kit comprising the particulate composition, methods of making and using the particulate composition, and articles made from the bone graft substitute cement are also provided.

25 Claims, 5 Drawing Sheets

(56) References Cited

U.S. PATENT DOCUMENTS

| | | | |
|---|---|---|---|
| 4,959,104 A | 9/1990 | Iino et al. |
| 4,990,163 A | 2/1991 | Ducheyne et al. |
| 5,015,610 A | 5/1991 | Dwivedi |
| 5,017,518 A | 5/1991 | Hirayama et al. |
| 5,030,396 A | 7/1991 | Saita et al. |
| 5,071,434 A | 12/1991 | Tsuzuki et al. |
| 5,137,534 A | 8/1992 | Sumita |
| 5,149,368 A | 9/1992 | Liu et al. |
| 5,152,791 A | 10/1992 | Hakamatsnka et al. |
| 5,171,720 A | 12/1992 | Kawakami |
| 5,178,845 A | 1/1993 | Constantz et al. |
| 5,180,426 A | 1/1993 | Sumita |
| 5,192,325 A | 3/1993 | Kijima et al. |
| 5,211,664 A | 5/1993 | Tepic et al. |
| 5,262,166 A | 11/1993 | Liu et al. |
| 5,281,265 A | 1/1994 | Liu |
| 5,338,356 A | 8/1994 | Hirano et al. |
| 5,385,887 A | 1/1995 | Yim et al. |
| 5,397,759 A | 3/1995 | Torobin |
| 5,425,769 A | 6/1995 | Snyders, Jr. |
| 5,462,722 A | 10/1995 | Liu et al. |
| 5,531,794 A | 7/1996 | Takagi et al. |
| 5,573,771 A | 11/1996 | Geistlich et al. |
| 5,605,713 A | 2/1997 | Boltong |
| 5,614,206 A | 3/1997 | Randolph et al. |
| 5,624,674 A | 4/1997 | Seare, Jr. |
| 5,639,402 A | 6/1997 | Barlow et al. |
| 5,681,572 A | 10/1997 | Seare, Jr. |
| 5,681,873 A | 10/1997 | Norton et al. |
| 5,697,981 A | 12/1997 | Ison et al. |
| 5,707,962 A | 1/1998 | Chen et al. |
| 5,714,103 A | 2/1998 | Bauer et al. |
| 5,769,897 A | 6/1998 | Harle |
| 5,807,567 A | 9/1998 | Randolph et al. |
| 5,910,315 A | 6/1999 | Stevenson et al. |
| 5,914,133 A | 6/1999 | Tsujino |
| 5,948,428 A | 9/1999 | Lee et al. |
| 6,037,519 A | 3/2000 | McKay |
| 6,117,456 A | 9/2000 | Lee et al. |
| 6,136,029 A | 10/2000 | Johnson et al. |
| 6,214,368 B1 | 4/2001 | Lee et al. |
| 6,224,635 B1 | 5/2001 | Ricci et al. |
| 6,296,667 B1 | 10/2001 | Johnson et al. |
| 6,358,532 B2 | 3/2002 | Starling et al. |
| 6,425,949 B1 | 7/2002 | Lemaitre et al. |
| 6,527,810 B2 | 3/2003 | Johnson et al. |
| 6,537,589 B1 | 3/2003 | Chae et al. |
| 6,558,709 B2 | 5/2003 | Higham |
| 6,582,228 B2 | 6/2003 | Ricci et al. |
| 6,652,887 B1 | 11/2003 | Richelsoph et al. |
| 6,706,273 B1 | 3/2004 | Roessler |
| 6,716,216 B1 | 4/2004 | Boucher et al. |
| 6,733,582 B1 | 5/2004 | Bohner et al. |
| 6,793,725 B2 | 9/2004 | Chow et al. |
| 6,808,561 B2 | 10/2004 | Genge et al. |
| 6,822,033 B2 | 11/2004 | Yu et al. |
| 6,840,995 B2 | 1/2005 | Lin et al. |
| 6,849,275 B2 | 2/2005 | Higham |
| 6,949,251 B2 | 9/2005 | Dalal et al. |
| 6,953,594 B2 | 10/2005 | Lee et al. |
| 6,955,716 B2 | 10/2005 | Xu et al. |
| 6,994,726 B2 | 2/2006 | Lin et al. |
| 7,018,460 B2 | 3/2006 | Xu et al. |
| 7,066,999 B2 | 6/2006 | Lin et al. |
| 7,147,666 B1 | 12/2006 | Grisoni |
| 7,211,266 B2 | 5/2007 | Cole et al. |
| 7,250,550 B2 | 7/2007 | Overby et al. |
| 7,291,179 B2 | 11/2007 | Miller et al. |
| 7,294,187 B2 | 11/2007 | Chow et al. |
| 7,351,280 B2 | 4/2008 | Khairoun et al. |
| 7,357,941 B2 | 4/2008 | Dalal et al. |
| 7,390,498 B2 | 6/2008 | Dalal et al. |
| 7,393,405 B2 | 7/2008 | Bohner |
| 7,407,542 B2 | 8/2008 | Lemaitre et al. |
| 7,417,077 B2 | 8/2008 | Lidgren et al. |
| 7,507,257 B2 | 3/2009 | Cole et al. |
| 7,553,362 B2 | 6/2009 | Lu et al. |
| 7,658,768 B2 | 2/2010 | Miller et al. |
| 7,670,419 B2 | 3/2010 | Bohner |
| 7,709,029 B2 | 5/2010 | Chow et al. |
| 7,754,246 B2 * | 7/2010 | Moseley ............... A61L 27/12 424/602 |
| 7,766,972 B2 | 8/2010 | Overby et al. |
| 7,938,572 B2 | 5/2011 | Lidgren et al. |
| 7,972,630 B2 | 7/2011 | Lidgren |
| 7,976,874 B2 | 7/2011 | Lin et al. |
| 8,025,903 B2 | 9/2011 | Moseley et al. |
| 8,029,755 B2 | 10/2011 | Ahn |
| 8,168,692 B2 | 5/2012 | Wenz |
| 8,173,149 B2 | 5/2012 | Dalal et al. |
| 8,221,781 B2 | 7/2012 | Rosenberg et al. |
| 8,282,396 B2 | 10/2012 | Chow et al. |
| 8,297,831 B2 | 10/2012 | Lidgren et al. |
| 8,357,364 B2 | 1/2013 | Kumta et al. |
| 8,414,930 B2 | 4/2013 | Liu et al. |
| 8,420,127 B2 | 4/2013 | Lidgren et al. |
| 8,435,343 B2 | 5/2013 | Yahav et al. |
| 8,454,988 B2 | 6/2013 | Rosenberg et al. |
| 8,557,235 B2 | 10/2013 | Kumta et al. |
| 8,586,101 B2 | 11/2013 | Lidgren |
| 8,597,604 B2 | 12/2013 | Ahn |
| 8,657,952 B2 | 2/2014 | Cole et al. |
| 8,662,737 B2 | 3/2014 | Lidgren et al. |
| 8,685,464 B2 | 4/2014 | Moseley et al. |
| 8,685,465 B2 | 4/2014 | Moseley et al. |
| 8,784,551 B2 | 7/2014 | Ju et al. |
| 9,180,224 B2 * | 11/2015 | Moseley ............... A61L 27/12 |
| 9,446,170 B2 * | 9/2016 | Moseley ............... C04B 28/34 |
| 2001/0018614 A1 | 8/2001 | Bianchi |
| 2001/0031799 A1 | 10/2001 | Shimp |
| 2002/0016636 A1 | 2/2002 | Ricci et al. |
| 2002/0055143 A1 | 5/2002 | Bell et al. |
| 2002/0169066 A1 | 11/2002 | Cassidy et al. |
| 2002/0197315 A1 | 12/2002 | Haggard et al. |
| 2003/0049328 A1 | 3/2003 | Dalal et al. |
| 2003/0050710 A1 | 3/2003 | Petersen et al. |
| 2003/0055512 A1 | 3/2003 | Genin et al. |
| 2003/0161852 A1 | 8/2003 | Miller et al. |
| 2003/0167093 A1 | 9/2003 | Xu et al. |
| 2003/0185903 A1 | 10/2003 | Cole et al. |
| 2003/0216777 A1 | 11/2003 | Tien et al. |
| 2004/0024081 A1 | 2/2004 | Trieu et al. |
| 2004/0137032 A1 | 7/2004 | Wang |
| 2004/0220681 A1 | 11/2004 | Cole et al. |
| 2004/0244651 A1 | 12/2004 | Lemaitre et al. |
| 2005/0031704 A1 | 2/2005 | Ahn |
| 2005/0042210 A1 | 2/2005 | Akai |
| 2005/0074415 A1 | 4/2005 | Chow et al. |
| 2005/0076813 A1 | 4/2005 | Lin et al. |
| 2005/0081750 A1 | 4/2005 | Xu et al. |
| 2005/0084542 A1 | 4/2005 | Rosenberg et al. |
| 2005/0119746 A1 | 6/2005 | Lidgren |
| 2005/0170012 A1 | 8/2005 | Dalal et al. |
| 2005/0184418 A1 | 8/2005 | Lin et al. |
| 2005/0186353 A1 | 8/2005 | Lin et al. |
| 2005/0186449 A1 | 8/2005 | Lin et al. |
| 2005/0251149 A1 | 11/2005 | Wenz |
| 2005/0268819 A1 | 12/2005 | Lin et al. |
| 2006/0096540 A1 | 5/2006 | Choi |
| 2006/0213398 A1 | 9/2006 | Barralet et al. |
| 2006/0292200 A1 | 12/2006 | Delaney |
| 2007/0026030 A1 | 2/2007 | Gill et al. |
| 2007/0059281 A1 | 3/2007 | Moseley et al. |
| 2007/0166394 A1 | 7/2007 | Yeh |
| 2008/0014242 A1 | 1/2008 | Overby et al. |
| 2008/0020349 A1 | 1/2008 | Dricot |
| 2009/0018667 A1 | 1/2009 | Lidgren et al. |
| 2009/0192629 A1 | 7/2009 | Lidgren et al. |
| 2009/0220475 A1 | 9/2009 | Bohner et al. |
| 2010/0154681 A1 | 6/2010 | Yeh |
| 2010/0185200 A1 | 7/2010 | Dricot |
| 2011/0208305 A1 | 8/2011 | Malinin et al. |
| 2012/0045484 A1 | 2/2012 | Cooper |
| 2012/0061285 A1 | 3/2012 | Moseley et al. |

(56) References Cited

U.S. PATENT DOCUMENTS

| | | | |
|---|---|---|---|
| 2012/0129761 A1 | 5/2012 | Sandell et al. |
| 2012/0191214 A1 | 7/2012 | Nies |
| 2012/0195982 A1 | 8/2012 | Hu et al. |
| 2013/0059013 A1 | 3/2013 | Vitale Brovarone et al. |
| 2013/0101673 A1 | 4/2013 | Borden |
| 2013/0138114 A1 | 5/2013 | Lin et al. |
| 2013/0295193 A1 | 11/2013 | Chern-Lin et al. |
| 2014/0012271 A1 | 1/2014 | Steckel et al. |
| 2014/0067082 A1 | 3/2014 | Liu et al. |
| 2014/0128990 A1 | 5/2014 | Farrar et al. |
| 2014/0134227 A1 | 5/2014 | Cole et al. |

FOREIGN PATENT DOCUMENTS

| | | | |
|---|---|---|---|
| CN | 102600513 A | | 7/2012 |
| CN | 103349793 A | | 10/2013 |
| EP | 0 263 489 A1 | | 4/1988 |
| EP | 0 335 359 A2 | | 11/1989 |
| JP | H01-107769 A | | 4/1989 |
| JP | 10 151188 | | 6/1998 |
| JP | 2009-507575 A | | 2/2009 |
| JP | 2012-524821 A | | 10/2012 |
| KR | 101270876 B1 | | 6/2013 |
| RU | 2 236 216 C1 | | 9/2004 |
| WO | WO 91/00252 A1 | | 1/1991 |
| WO | WO 91/17722 A1 | | 11/1991 |
| WO | WO 00/74690 A1 | | 12/2000 |
| WO | WO 01/10463 A1 | | 2/2001 |
| WO | WO 03/024316 A2 | | 3/2003 |
| WO | WO 03/082365 A1 | | 10/2003 |
| WO | WO 2004/069396 A1 | | 8/2004 |
| WO | WO 2004/103419 A1 | | 12/2004 |
| WO | WO 2005/084591 A1 | | 9/2005 |
| WO | WO 2010/024549 A2 | | 3/2010 |
| WO | WO 2010/073860 | | 7/2010 |
| WO | WO 2010/117346 A2 | | 10/2010 |
| WO | WO 2011/098438 A1 | | 8/2011 |
| WO | WO 2012/039592 A1 | | 3/2012 |
| WO | WO 2013/093439 A1 | | 6/2013 |
| WO | WO 2014/009674 A1 | | 1/2014 |

OTHER PUBLICATIONS

Grimandi et al. "In vitro Evaluation of a New Injectable Calcium Phosphate Material," J Biomed Mater Res, 1998, pp. 660-666, vol. 39.

[No Author Listed] Accession No. 2008-B52078. Database WPI. Aug. 22, 2007, 1 page.

[No Author Listed] Accession No. CN-200710063903-A. Database EPODOC. Aug. 22, 2007, 2 page.

[No Author Listed] STN—International Accession No. 160:550679 CA. Chemical Abstracts Service. May 1, 2014. Mao et al., Preparation and properties of α-calcium sulphate hemihydrate and β-tricalcium phosphate bone substitute. Bio-Medical Materials and Engineering. 2 pages.

Ikenaga et al., Biomechanical characterization of a biodegradable calcium phosphate hydraulic cement: A comparison with porous biphasic calcium phosphate ceramics. Journal of Biomedical Material Research. 1998;40(1):139-44.

Mao et al., Preparation and properties of α-calcium sulphate hemihydrate and β-tricalcium phosphate bone substitute. Bio-Medical Materials and Engineering. 2013;23(3):197-210.

Mao et al., The Preparation and Evaluation of α-CSH/β-TCP Combined Artificial Bone. Advanced Materials Research. 2012;340:81-87).

PCT/US2014/069963, Mar. 10, 2015, International Search Report and Written Opinion.

PCT/US2014/069963, Dec. 2, 2015, International Preliminary Report on Patentability.

* cited by examiner

MULTIPHASIC BONE GRAFT SUBSTITUTE MATERIAL

CROSS-REFERENCE TO RELATED APPLICATIONS

This Application is a Continuation of U.S. Application Ser. No. 14/568,773, filed Dec. 12, 2014, entitled "Multiphasic Bone Graft Substitute Material" which claims priority under 35 U.S.C. § 119(e) to U.S. Provisional Application Ser. No. 62/031,635, filed Jul. 31, 2014, entitled "Multiphasic Bone Graft Substitute Material" and U.S. Provisional Application Ser. No. 61/915,837, filed Dec. 13, 2013, entitled "Multiphasic Bone Graft Substitute Material", each of which is incorporated herein by reference in its entirety for all purposes.

FIELD OF THE INVENTION

The invention is directed to a particulate composition adapted for forming a bone graft substitute cement upon mixing with an aqueous solution, a bone graft substitute cement made therefrom, a bone graft substitute kit comprising the particulate composition, methods of making and using the particulate composition, and articles made from the bone graft substitute cement.

BACKGROUND OF THE INVENTION

Defects in bone structure arise in a variety of circumstances, such as trauma, disease, and surgery. There is a need for effective repair of bone defects in various surgical fields, including maxillo-craniofacial, periodontics, and orthopedics. Numerous natural and synthetic materials and compositions have been used to stimulate healing at the site of a bone defect. As with compositions used to repair other types of tissue, the biological and mechanical properties of a bone repair material are critical in determining the effectiveness and suitability of the material in any particular application.

After blood, bone is the second most commonly transplanted material. Autologous cancellous bone has long been considered the most effective bone repair material, since it is both osteoinductive and non-immunogenic. However, adequate quantities of autologous cancellous bone are not available under all circumstances, and donor site morbidity and trauma are serious drawbacks to this approach. The use of allograft bone avoids the problem of creating a second surgical site in the patient, but suffers from some disadvantages of its own. For instance, allograft bone typically has a lower osteogenic capacity than autograft bone, a higher resorption rate, creates less revascularization at the site of the bone defect, and typically results in a greater immunogenic response. The transfer of certain diseases is also a danger when using allografts.

To avoid the problems associated with autograft and allograft bone, considerable research has been conducted in the area of synthetic bone substitute materials that can be used in lieu of natural bone. For example, various compositions and materials comprising demineralized bone matrix, calcium phosphate, and calcium sulfate have been proposed.

Cements comprising calcium sulfate have a long history of use as bone graft substitutes. Modern surgical grade calcium sulfate cements offer high initial strength, good handling properties, and are consistently replaced by bone in many applications. However, calcium sulfate cements are characterized by relatively rapid resorption by the body, which can be undesirable in certain applications.

Hydroxyapatite is one of the most commonly used calcium phosphates in bone graft materials. Its structure is similar to the mineral phase of bone and it exhibits excellent biocompatibility. However, hydroxyapatite has an extremely slow resorption rate that may be unsuitable in certain applications. Other calcium phosphate materials have also been used in the art, such as β-tricalcium phosphate, which exhibits a faster resorption rate than hydroxyapatite, but has less mechanical strength. Certain calcium phosphate materials that set in situ have also been attempted, such as mixtures of tetracalcium phosphate and dicalcium phosphate anhydrate or dihydrate, which react to form hydroxyapatite when mixed with an aqueous solution.

The presently available synthetic bone repair materials do not present ideal functional characteristics for all bone graft applications. As noted above, some compositions exhibit a resorption rate that is either too slow or too rapid. Further, many bone graft cements are difficult to implant because they fail to set or cannot be injected. Other drawbacks are inadequate strength and difficulty in adding biologically active substances for controlled release. Furthermore, certain bone graft cements developed to address these concerns fail to completely set (harden) in the presence of particular additives. For these reasons, there remains a need in the art for bone graft cement compositions that combine a desirable resorption rate with high mechanical strength, ease of handling, osteoconductivity, and workable set time even in the presence of additives.

BRIEF SUMMARY OF THE INVENTION

The present invention provides a particulate composition adapted for forming a bone graft substitute cement upon mixing with an aqueous solution, as well as a hardened bone graft substitute cement made therefrom. The invention also relates to kits comprising the particulate composition, and methods of making and using the composition. In some embodiments, the particulate composition of the invention comprises a calcium sulfate hemihydrate powder in combination with calcium phosphate granules with a porous morphology, and typically also in combination with a brushite-forming calcium phosphate mixture. Upon mixing the particulate composition with an aqueous mixing solution, a hardened triphasic cement comprising brushite and calcium sulfate dihydrate is typically formed. The calcium sulfate dihydrate provides good mechanical strength and, due to its relatively fast resorption rate, is rapidly replaced with bone tissue in the resulting cement, while the brushite serves to reduce the overall resorption rate of the cement as compared to a cement composition solely comprising calcium sulfate dihydrate. Certain embodiments of the bone substitute cement of the invention exhibit high mechanical strength, such as high compressive strength and diametral tensile strength, set into a hardened composition within a reasonable period of time, facilitate development of high quality bone at the site of the bone defect, and exhibit acceptable handling characteristics. In certain embodiments, the bone substitute cement of the invention is capable of hardening and setting in the presence of biological additives.

In one aspect of the present invention is provided a particulate composition adapted for forming a bone graft substitute cement upon mixing with an aqueous solution, comprising: i) a calcium sulfate hemihydrate powder, wherein the calcium sulfate hemihydrate is present at a concentration of at least about 50 weight percent based on the total weight of the particulate composition; ii) a monocalcium phosphate monohydrate powder; iii) a non-porous β-tricalcium phosphate powder; and iv) a porous β-tricalcium phosphate powder.

The calcium sulfate hemihydrate can be, for example, α-calcium sulfate hemihydrate. In certain embodiments, the calcium sulfate hemihydrate is present at a concentration of at least about 70 weight percent based on the total weight of the particulate composition. The calcium sulfate hemihydrate can, in certain embodiments, have a bimodal particle distribution. The calcium sulfate hemihydrate may have a median particle size of about 5 microns to about 20 microns, for example. In some embodiments, the calcium sulfate hemihydrate has a bimodal particle distribution comprising about 30 to about 60 volume percent of particles having a mode of about 1.0 to about 3.0 microns and about 40 to about 70 volume percent of particles having a mode of about 20 to about 30 microns, based on the total volume of the calcium sulfate hemihydrate powder.

The porous β-tricalcium phosphate powder can be present, for example, at a concentration of between about 5 and about 15 weight percent. In some embodiments, the porous β-tricalcium phosphate powder exhibits a bimodal particle size distribution. For example, in certain embodiments, the porous β-tricalcium phosphate powder comprises less than 50% by weight of particles having a particle size up to about 63 microns and greater than 50% by weight of particles having a particle size greater than about 63 microns. In certain embodiments, the porous β-tricalcium phosphate powder comprises about 25% by weight of particles having a particle size up to about 63 microns and about 75% by weight of particles having a particle size greater than about 63 microns.

In certain embodiments, the pore sizes of the porous β-tricalcium phosphate powder are in the range of about 100 microns to about 400 microns. The porous β-tricalcium phosphate powder can, in some embodiments, be characterized by an interconnected, multidirectional porosity. The porosity of the porous β-tricalcium phosphate powder can vary and, in some embodiments, the porous β-tricalcium phosphate powder can have a total porosity of at least about 50%.

The non-porous β-tricalcium phosphate powder can have, for example, a median particle size of less than about 20 microns. In some embodiments, the non-porous β-tricalcium phosphate powder has a bimodal particle size distribution comprising about 30 to about 70 volume percent of particles having a mode of about 2.0 to about 6.0 microns and about 30 to about 70 volume percent of particles having a mode of about 40 to about 70 microns based on the total volume of the non-porous β-tricalcium phosphate powder. In some embodiments, the β-tricalcium phosphate powder has a bimodal particle size distribution comprising about 50 to about 65 volume percent of particles having a mode of about 4.0 to about 5.5 microns and about 35 to about 50 volume percent of particles having a mode of about 60 to about 70 microns based on the total volume of the non-porous β-tricalcium phosphate powder.

Various other components can be incorporated within the compositions described herein. For example, in some embodiments, the particulate composition can further comprise non-porous β-tricalcium phosphate granules having a median particle size of at least about 75 microns (e.g., having a median particle size of about 75 to about 1,000 microns). The non-porous β-tricalcium phosphate granules can be, for example, present at a concentration of up to about 20 weight percent based on the total weight of the particulate composition or present at a concentration of up to about 12 weight percent based on the total weight of the particulate composition.

The particulate composition can, in some embodiments, further comprise an accelerant adapted for accelerating the conversion of calcium sulfate hemihydrate to calcium sulfate dihydrate. For example, the accelerant can be selected from the group consisting of calcium sulfate dihydrate particles, potassium sulfate particles, and sodium sulfate particles, wherein the accelerant is optionally coated with sucrose. In some embodiments, the accelerant may be present at a concentration of up to about 1 weight percent based on the total weight of the particulate composition.

In one specific embodiment is provided a particulate composition adapted for forming a bone graft substitute cement upon mixing with an aqueous solution, comprising: i) a calcium sulfate hemihydrate powder having a bimodal particle distribution and a median particle size of about 5 to about 20 microns, wherein the calcium sulfate hemihydrate is present at a concentration of at least about 70 weight percent based on the total weight of the particulate composition; ii) a monocalcium phosphate monohydrate powder; iii) a non-porous β-tricalcium phosphate powder having a median particle size of less than about 20 microns, the monocalcium phosphate monohydrate powder and the non-porous β-tricalcium phosphate powder being present at a combined concentration of about 3 to about 20 weight percent based on the total weight of the particulate composition; iv) non-porous β-tricalcium phosphate granules having a median particle size of at least about 75 microns and present at a concentration of up to about 20 weight percent based on the total weight of the particulate composition; v) porous β-tricalcium phosphate powder, in an amount of up to about 15 weight percent based on the total weight of the particulate composition; and vi) an accelerant adapted for accelerating the conversion of calcium sulfate hemihydrate to calcium sulfate dihydrate, the accelerant being present at a concentration of up to about 1 weight percent based on the total weight of the particulate composition.

In another specific embodiment is provided a particulate composition adapted for forming a bone graft substitute cement upon mixing with an aqueous solution, comprising: i) an α-calciumsulfate hemihydrate powder having a bimodal particle distribution and a median particle size of about 5 to about 20 microns, wherein the calcium sulfate hemihydrate is present at a concentration of at least about 70 weight percent based on the total weight of the particulate composition, and wherein the calcium sulfate hemihydrate powder has a bimodal particle distribution comprising about 30 to about 60 volume percent of particles having a mode of about 1.0 to about 3.0 microns and about 40 to about 70 volume percent of particles having a mode of about 20 to about 30 microns, based on the total volume of the calcium sulfate hemihydrate powder; ii) a monocalcium phosphate monohydrate powder; iii) a β-tricalcium phosphate powder having a median particle size of less than about 20 microns, the monocalcium phosphate monohydrate powder and the β-tricalcium phosphate powder being present at a combined concentration of about 3 to about 20 weight percent based on the total weight of the particulate composition; iv)β-tricalcium phosphate granules having a median particle size of about 100 to about 400 microns and present at a concentration of up to about 12 weight percent based on the total weight of the particulate composition; v) porous β-tricalcium phosphate powder, in an amount of up to about 15 weight percent based on the total weight of the particulate composition, wherein the porous β-tricalcium phosphate powder comprises less than 50% by weight of particles having a particle size up to about 63 microns and greater than 50% by weight of particles having a particle size greater than about 63 microns; and vi) an accelerant adapted for accelerating the conversion of calcium sulfate hemihydrate to calcium sulfate dihydrate, the accelerant being present at a concentration of up to about 1 weight percent based on the total weight of the particulate composition.

The particulate compositions described herein can, in some embodiments, further comprise a biologically active agent. Exemplary biologically active agents that can be useful in the compositions include, but are not limited to, the group consisting of cancellous bone chips, growth factors, antibiotics, pesticides (e.g., antifungal agents and antiparasitic agents), chemotherapeutic agents, antivirals, analgesics, and anti-inflammatory agents. In some embodiments, the optional biologically active agent comprises bone marrow aspirate. In some embodiments, the optional biologically active agent comprises a growth factor selected from the group consisting of fibroblast growth factors, platelet-derived growth factors, bone morphogenic proteins, osteogenic proteins, transforming growth factors, LIM mineralization proteins, osteoid-inducing factors, angiogenins, endothelins; growth differentiation factors, ADMP-1, endothelins, hepatocyte growth factor and keratinocyte growth factor, heparin-binding growth factors, hedgehog proteins, interleukins, colony-stimulating factors, epithelial growth factors, insulin-like growth factors, cytokines, osteopontin, and osteonectin.

The properties of the particulate compositions described herein upon mixing with an aqueous solution can vary. For example, in some embodiments, the particulate composition has a Vicat set time upon mixing with an aqueous solution of about 3 to about 8 minutes. In some embodiments, the particulate composition has a Gillmore set time upon mixing with an aqueous solution of about 6 to about 20 minutes.

In another aspect of the invention is provided a bone graft substitute cement comprising the reaction product formed by mixing a particulate composition as described herein with an aqueous solution, the reaction product comprising calcium sulfate dihydrate, brushite, and a porous β-tricalcium phosphate component. In some embodiments, the bone graft substitute cement can further comprise non-porous β-tricalcium phosphate granules. The cement can, in some embodiments, be cast in a predetermined shape (e.g., including, but not limited to, a pellet, granule, wedge, block, or disk). The makeup of the aqueous solution with which the particulate compositions are mixed can vary. For example, in some embodiments, the aqueous solution comprises a carboxylic acid (e.g., including, but not limited to, a hydroxy carboxylic acid, such as glycolic acid). In some embodiments, the carboxylic acid can be neutralized to a pH of about 6.5 to about 7.5. In certain embodiments, the aqueous solution further comprises sodium chloride. For example, in some embodiments, the aqueous solution comprises both a carboxylic acid and sodium chloride.

In another aspect of the present invention is provided a bone graft substitute kit, comprising one or more containers enclosing a particulate composition as described herein, a separate container enclosing a sterile aqueous solution, and a written instruction set describing a method of using the kit. The bone graft substitute kit may optionally further comprise a mixing apparatus adapted for mixing the particulate composition and the aqueous solution. The bone graft substitute kit may optionally further comprise a delivery device adapted for delivering a bone graft substitute cement mixture to the site of a bone defect, such as a Jamshidi needle.

In certain embodiments, a portion of the particulate composition is enclosed in a first syringe and a portion of the particulate composition is enclosed in a second syringe, and the kit further includes a syringe connector adapted to connect the first and second syringe such that the contents of each syringe can be mixed. In still further embodiments, the kit includes at least one syringe containing at least a portion of the particulate composition and a vial adaptor adapted to connect the syringe to the container enclosing the sterile aqueous solution.

In a still further aspect of the invention is provided a method for treating a bone defect, comprising applying a bone graft substitute cement as described herein to the site of the bone defect.

BRIEF DESCRIPTION OF THE DRAWINGS

Figure 1:
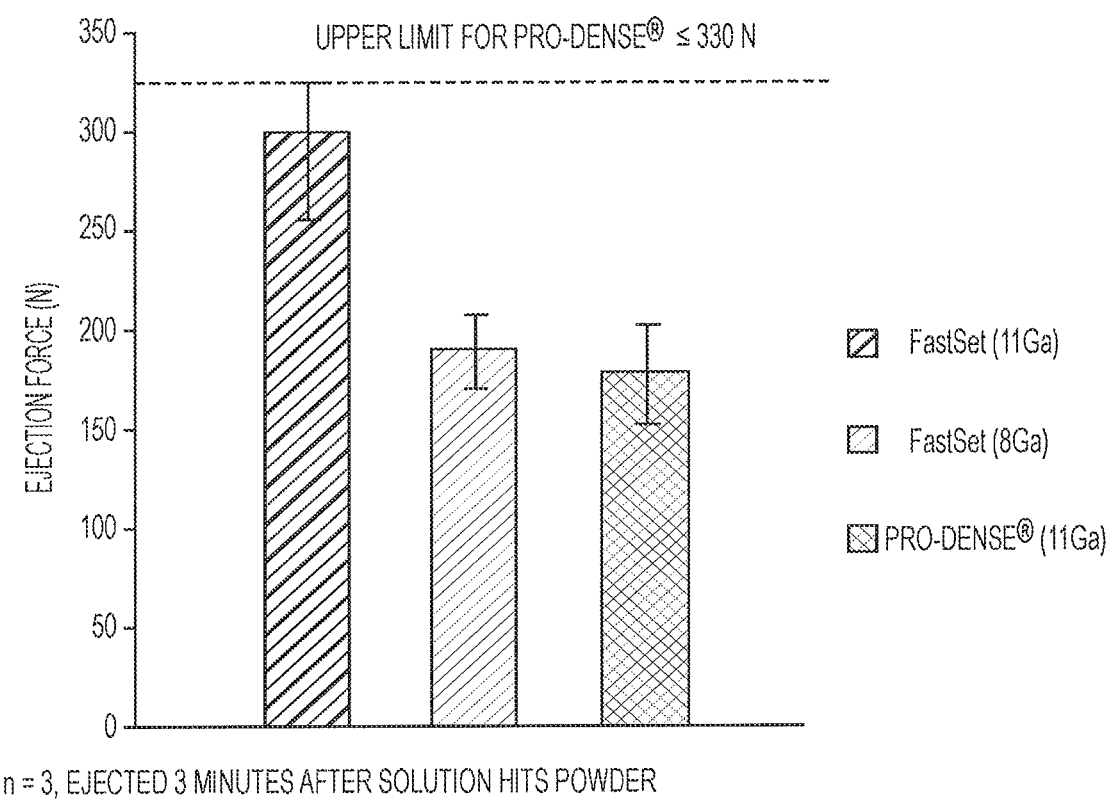
Figure 2:
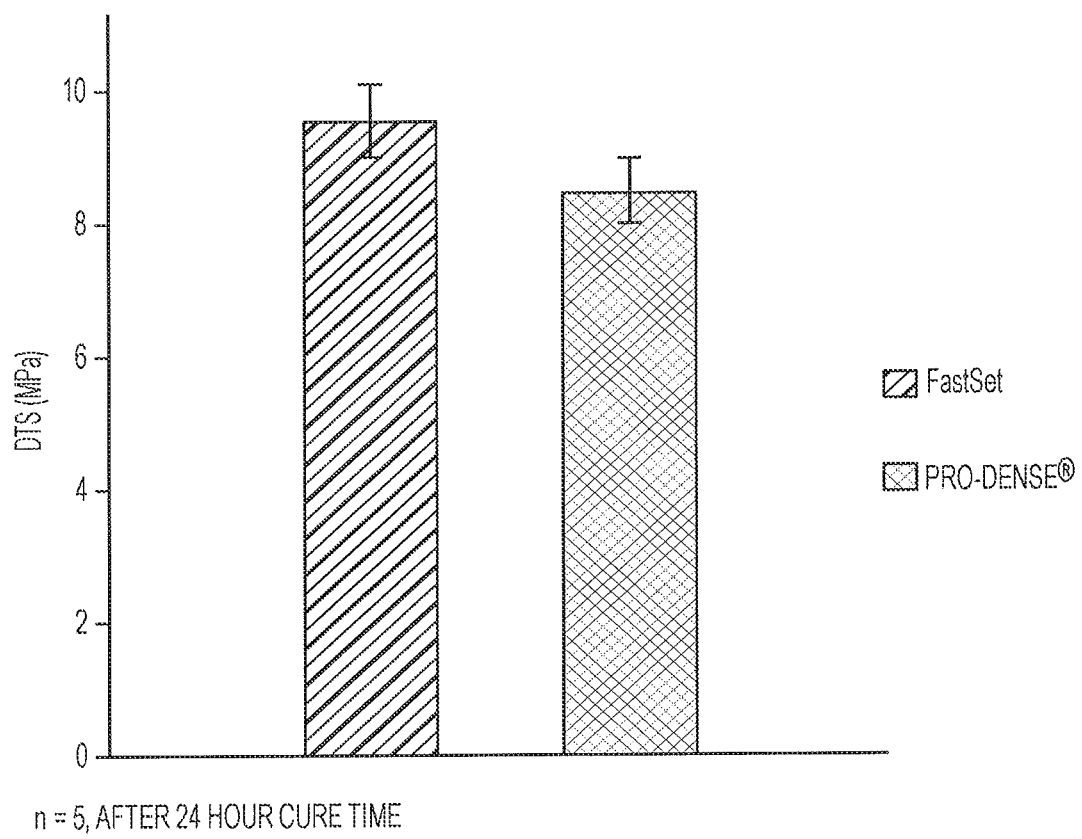
Figure 3:
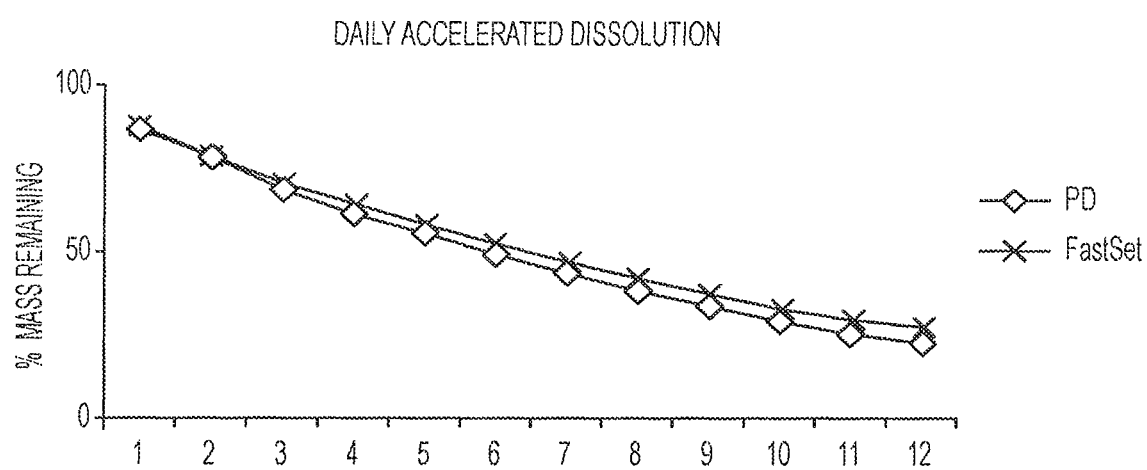
Figure 4:
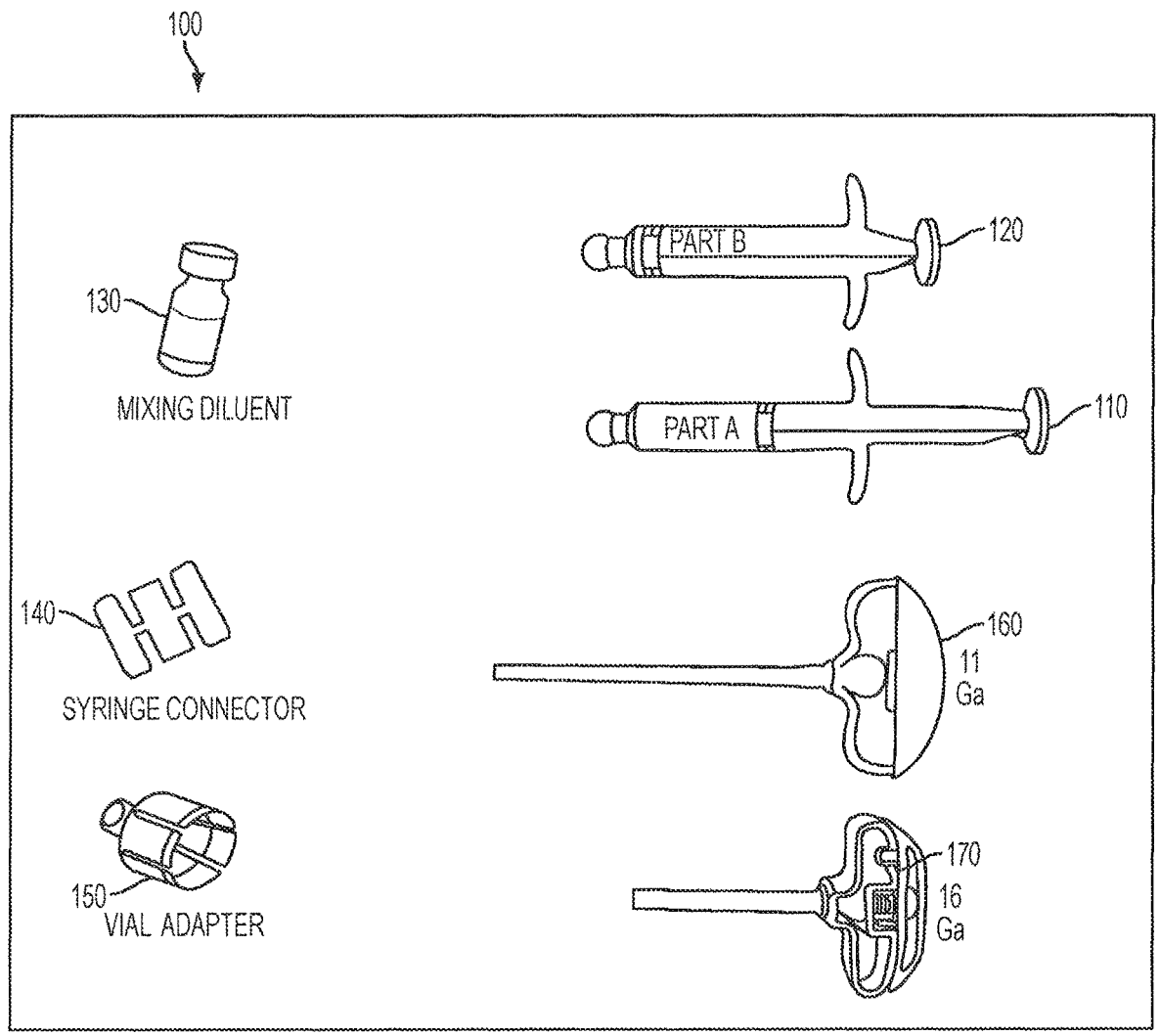
Figure 5:
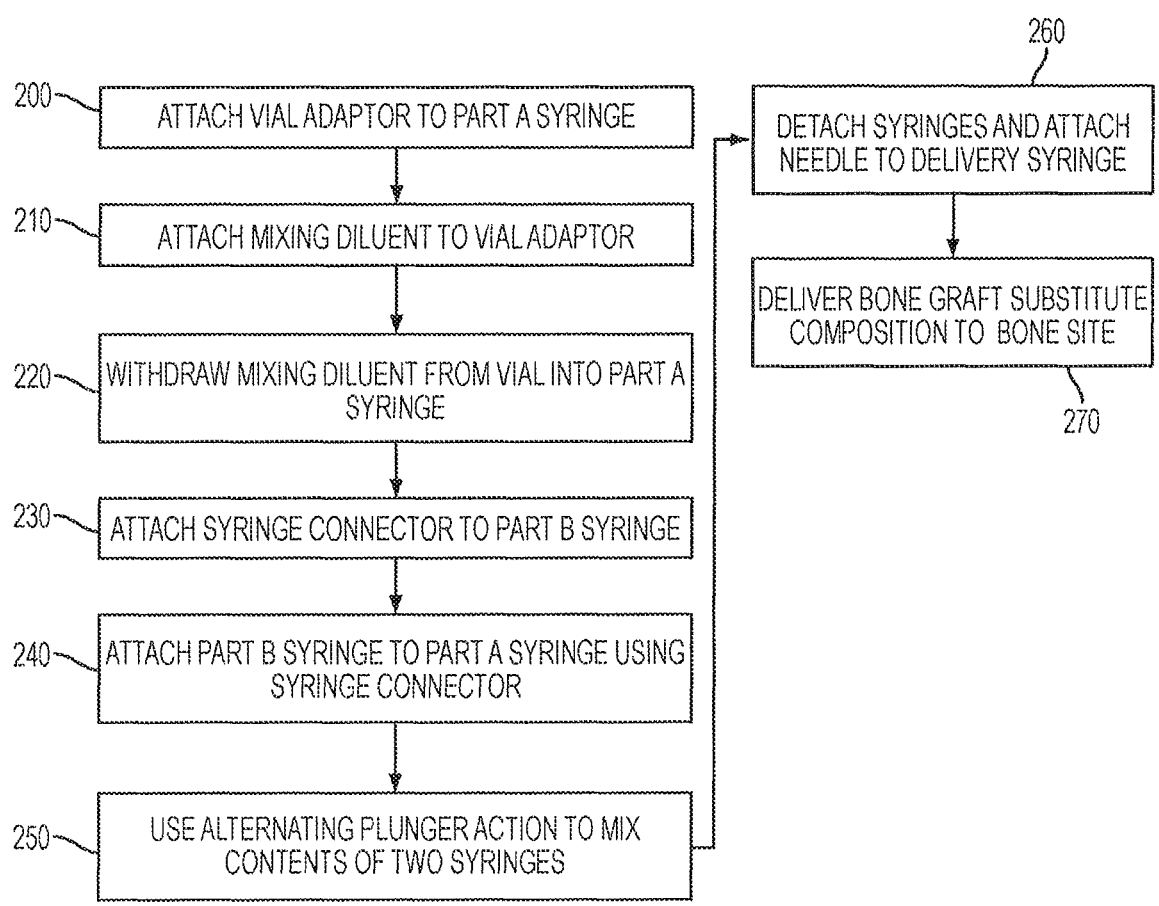

Having thus described the invention in general terms, reference will now be made to the accompanying drawings, wherein:

FIG. 1 is a graph comparing the ejective force of an inventive bone graft cement composition and a control composition;

FIG. 2 is a graph comparing the diametral tensile strength of an inventive bone graft cement composition and a control composition;

FIG. 3 is a graph comparing the daily accelerated in vitro dissolution properties of an inventive bone graft cement composition and a control composition;

FIG. 4 is an example of a bone graft substitute kit of the present invention; and FIG. 5 illustrates a method of preparing a bone graft substitute composition using the kit of FIG. 4.

DETAILED DESCRIPTION OF THE INVENTION

The present inventions now will be described more fully hereinafter with reference to the accompanying drawings. The invention may be embodied in many different forms and should not be construed as limited to the embodiments set forth herein; rather, these embodiments are provided so that this disclosure will satisfy applicable legal requirements. As used in this specification and the claims, the singular forms "a," "an," and "the" include plural referents unless the context clearly dictates otherwise.

The present invention provides a particulate composition useful as a bone graft substitute cement that hardens or sets upon mixing with an aqueous solution. Advantageously, the particulate composition can provide a bone graft substitute cement with a set time that is faster than certain other commercially available bone graft substitute cements. The particulate composition includes a calcium sulfate hemihydrate (hereinafter "CSH") powder, a porous β-tricalcium phosphate (hereinafter "β-TCP") component, and optionally a brushite-forming calcium phosphate mixture comprising monocalcium phosphate monohydrate (hereinafter "MCPM") powder and a non-porous β-TCP powder. Certain components useful according to the present invention are described in U.S. Pat. Nos. 8,025,903 and 7,754,246 to Moseley et al. and U.S. Patent Application Publication No. 2007/0128248 to Moseley et al., which are all incorporated herein by reference.

Use of the particulate composition of the invention produces a bone graft substitute cement comprising calcium sulfate dihydrate (hereinafter "CSD"), which is the product of the reaction between CSH and water. The CSD component of the cement confers good mechanical strength to the cement, stimulates bone growth, and provides a relatively fast resorption rate in vivo, such that a porous structure in the cement is quickly created upon implantation. Thus, the CSD component of the cement can be rapidly replaced with bone tissue ingrowth into the implant site.

Certain preferred components of the composition (e.g., MCPM, non-porous β-TCP granules, and/or non-porous β-TCP powder) can react, at least in part, to form brushite upon mixing with an aqueous solution. The presence of the brushite in the cement slows the resorption rate of the bone graft substitute cement as compared to a cement comprising CSD only. Thus, the bone graft substitute cement of the invention provides a triphasic resorption defined by the CSD component, the TCP component and the brushite component.

In addition to a relatively slow resorption rate, embodiments of the particulate composition of the invention can provide a bone graft substitute cement that exhibits high mechanical strength, good handling characteristics, and a reasonable setting time, particularly a setting time that is somewhat faster than certain other commercially available bone graft substitute cements. Additionally, certain embodiments of the bone graft substitute cement of the invention are capable of producing high quality bone when used to treat bone defects. Furthermore, certain embodiments described herein are uniquely able to set in the presence of biologically active agents.

The CSH powder used in the present invention preferably has a bimodal particle distribution. As understood in the art, a bimodal particle distribution refers to a particle distribution characterized by two peaks in a plot of particle size vs. the volume percentage of particles of each size. In a preferred embodiment, the bimodal particle distribution of the CSH powder is characterized by about 30 to about 60 volume percent of particles having a mode of about 1.0 to about 3.0 microns and about 40 to about 70 volume percent of particles having a mode of about 20 to about 30 microns, based on the total volume of the CSH powder. In yet another embodiment, the bimodal particle distribution comprises about 40 to about 60 volume percent of particles having a mode of about 1.0 to about 2.0 microns and about 40 to about 60 volume percent of particles having a mode of about 20 to about 25 microns. The median particle size of the CSH powder is preferably about 5 to about 20 microns, more preferably about 8 to about 15 microns, and most preferably about 10 to about 15 microns.

As used herein, "median particle size" refers to the particle size that divides a population of particles in half such that half of the volume of particles in the population is above the median size and half is below. Median particle size is measured using linear interpolation of data acquired through a high resolution laser diffraction method. More specifically, the laser diffraction method is performed with parallel light with a constant frequency of 632.8 nanometers and which exhibits 5 milliwatts of power. Measurements of laser diffraction are acquired through a 32 channel detector array. Particle delivery to measurement system is performed through a relatively constant mass flow rate using an optimum dispersing media such as air flow creating a −3.5 bar gauge pressure. A commercially available machine for laser-diffraction particle analysis is the OASIS (Sympatec; Clausthal-Zellerfeld, Germany) dispersing unit. The OASIS system is used in the dry mode via the VIBRI model HDD200 and RODOS M. The VIBRI model is used with a 75% feed rate and 3.0 mm gap. The −3.5 bar gauge pressure is produced through a 4 mm injector. For measuring particle size of calcium sulfate hemihydrate, the R2 lens (0.25/0.45 . . . 87.5 microns) is preferred, and for tricalcium phosphate components, the R4 lens (0.5/1.8 . . . 350 microns) is preferred (both also from Sympatec).

The particulate composition in the invention preferably comprises a CSH powder in an amount of at least about 50 weight percent based on the total weight of the particulate composition, more preferably at least about 60 weight percent, and most preferably at least about 70 weight percent. Typically, the CSH powder is present in an amount of about 70 weight percent to about 99 weight percent, more preferably about 70 weight percent to about 90 weight percent, and most preferably about 70 weight percent to about 80 weight percent (e.g., between about 70 weight percent and about 75 weight percent).

The CSH is preferably α-calcium sulfate hemihydrate, which exhibits higher mechanical strength as compared to the beta form upon setting to form CSD. The CSH portion of the particulate composition is important for providing mechanical strength to the resulting bone graft substitute cement, as well as contributing to the ability to set or harden in a relatively short period of time. As is known in the art, CSH has the formula $CaSO_4 \cdot \frac{1}{2}H_2O$, and will react with water to form calcium sulfate dihydrate ($CaSO_4 \cdot 2H_2O$). It is believed that the presence of CSD in the bone graft substitute cement of the invention contributes to rapid regeneration of bone tissue at the site of the bone defect.

CSH powder can be formed by dehydration of the dihydrate form by heating. Depending on the method of heating, the alpha or beta form is obtained. The two forms exhibit crystallographic and particle morphology differences. The preferred alpha form, which has a higher density, is typically characterized by large, hexagonal shaped rod-like primary crystals that are compact and well formed with sharp edges.

In a preferred embodiment, the CSH powder is made by the process disclosed in U.S. Pat. No. 2,616,789, which is incorporated entirely herein by reference in its entirety. The process involves immersion of calcium sulfate dihydrate in a solution of water and an inorganic salt. Preferred salts include magnesium chloride, calcium chloride, and sodium chloride. However, other inorganic salts can be used without departing from the invention, such as ammonium chloride, ammonium bromide, ammonium iodide, ammonium nitrate, ammonium sulfate, calcium bromide, calcium iodide, calcium nitrate, magnesium bromide, magnesium iodide, magnesium nitrate, sodium bromide, sodium iodide, sodium nitrate, potassium chloride, potassium bromide, potassium iodide, potassium nitrate, cesium chloride, cesium nitrate, cesium sulfate, zinc chloride, zinc bromide, zinc iodide, zinc nitrate, zinc sulfate, cupric chloride, cupric bromide, cupric nitrate, cupric sulfate, and mixtures thereof. Preferred salts are biocompatible, and any of the salts can be used in their anhydrous or hydrate forms. Reference to the salt is intended to encompass both anhydrous and hydrate forms. The calcium sulfate dihydrate and the solution are heated to substantially the boiling point at atmospheric pressure until a substantial portion of the calcium sulfate dihydrate is converted to CSH. The resulting CSH has a different crystalline structure than CSH produced by other hydrothermal processes and has a lower water-carrying capacity after being milled. In particular, the crystalline structure of the CSH made according to this method is characterized by thick, stubby, rod-like crystals.

In one embodiment, the CSH powder further includes an accelerant capable of accelerating the conversion of CSH to the dihydrate form, thereby causing the bone graft substitute cement made therefrom to set more quickly. Although not wishing to be bound by a theory of operation, it is believed that the accelerant particles act as crystallization nucleation sites for the conversion of CSH to calcium sulfate dihydrate. Examples of accelerants include calcium sulfate dihydrate, potassium sulfate, sodium sulfate, or other ionic salts. A preferred accelerant is calcium sulfate dihydrate crystals (available from U.S. Gypsum) coated with sucrose (available from VWR Scientific Products). A process of stabilizing the dihydrate crystals by coating with sucrose is described in U.S. Pat. No. 3,573,947, which is hereby incorporated by reference in its entirety. The accelerant is typically present in an amount of up to about 1.0 weight percent, based on the total weight of the particulate composition. In some embodiments, the particulate composition includes between about 0.001 and about 0.5 weight percent of the accelerant, more typically between about 0.01 and about 0.3 weight percent (e.g., between about 0.05 and about 0.15 weight percent). Mixtures of two or more accelerants can be used.

The non-porous calcium phosphate portion of the particulate composition of the invention typically comprises a MCPM powder ($Ca(H_2PO_4)_2 \cdot H_2O$) and non-porous β-TCP powder ($Ca_3(PO_4)_2$). As understood in the art, the main reaction product of MCPM and the non-porous β-TCP powder is brushite, otherwise known as dicalcium phosphate dihydrate ($CaHPO_4 \cdot 2H_2O$) (DCPD). The brushite-forming materials may also participate in other reactions that would result in the formation of certain calcium phosphates with a greater thermodynamic stability than DCPD, such as hydroxyapatite, octacalcium phosphate, and the like. A certain amount of the non-porous β-TCP powder may also remain unreacted in the cement. In certain embodiments of the invention, one or both of the brushite-forming components are not included in the inventive composition.

The non-porous β-TCP powder component preferably has a median particle size of less than about 35 microns, and more preferably a median particle size of less than about 30 microns, and most preferably a median particle size of less than about 25 microns. Typically the non-porous β-TCP powder will have a median particle size of about 10 microns to about 30 microns (e.g., around 20 microns). The size of the non-porous β-TCP powder may affect the amount of brushite formed in the bone graft substitute cement. It is believed that smaller particle sizes of non-porous β-TCP will result in an increased rate of brushite formation, and larger particle sizes will result in a lower rate of brushite formation. It is typically preferred to use smaller non-porous β-TCP particles in order to increase the brushite-forming reaction rate.

The non-porous β-TCP powder portion of the particulate composition preferably has a bimodal particle size distribution characterized by about 30 to about 70 volume percent of particles having a mode of about 2.0 to about 6.0 microns and about 30 to about 70 volume percent of particles having a mode of about 40 to about 70 microns based on the total volume of the β-tricalcium phosphate powder. In one embodiment, the non-porous β-TCP powder has a bimodal particle size distribution characterized by about 50 to about 65 volume percent of particles having a mode of about 4.0 to about 5.5 microns and about 35 to about 50 volume percent of particles having a mode of about 60 to about 70 microns based on the total volume of the non-porous β-tricalcium phosphate powder.

The MCPM powder is relatively soluble in water, which means particle size is relatively unimportant. Typically, the MCPM powder will have a particle size of less than about 350 microns; however, other particles sizes could be utilized without departing from the invention. As would be understood, MCPM is the hydrate form of monocalcium phosphate (MCP). As used herein, reference to MCPM is intended to encompass MCP, which is simply the anhydrous form of MCPM that releases the same number of calcium and phosphoric acid ions in solution. However, if MCP is used in place of MCPM, the amount of water used to form the bone graft substitute cement would need to be increased to account for the water molecule missing from MCP (if it is desired to produce precisely the same dissolution product as formed when using MCPM).

As noted above, the brushite component of the bone graft substitute cement of the invention serves to slow the in vivo resorption of the bone graft substitute cement as compared to a calcium sulfate cement. In turn, the slower resorption rate may enable the bone graft substitute cement to provide structural support at the site of the bone defect for longer periods of time, which can aid the healing process in certain applications. Although not bound by any particular theory of operation, it is believed that the bone graft substitute cement of the invention will become a highly porous matrix of calcium phosphate material after being administered in vivo due to the relatively quick resorption of the calcium sulfate component of the mixture. The remaining porous matrix of calcium phosphate provides excellent scaffolding for bone ingrowth during the natural healing process. The amount of MCPM powder and non-porous β-TCP powder present in the particulate composition can vary and depends primarily on the amount of brushite desired in the bone graft substitute cement. The brushite-forming calcium phosphate composition (i.e., the combined amount of MCPM and non-porous β-TCP powders) will typically be present at a concentration of about 3 to about 30 weight percent based on the total weight of the particulate composition, more preferably about 5 to about 10 weight percent, most preferably about 8 weight percent. The relative amounts of MCPM and non-porous β-TCP can be selected based on their equimolar, stoichiometric relationship in the brushite-forming reaction. In one embodiment, the MCPM powder is present at a concentration of about 2 to about 5 weight percent, based on the total weight of the particulate composition, and the non-porous β-TCP is present in an amount of about 3 to about 6 weight percent.

It has been discovered that the MCPM and non-porous β-TCP powders can react prematurely during storage in the presence of residual moisture to form brushite and/or monetite, an undesirable anhydrous analog of brushite. Thus, storage of the brushite-forming calcium phosphate powders together in a homogenous mixture can result in reduction in the amount of brushite produced upon mixing the particulate composition with the aqueous mixing solution to form the bone graft substitute cement, which in turn, can alter the properties of the bone graft substitute cement in an undesirable manner. As a result, in a preferred embodiment, the two calcium phosphate components are either packaged together in a dry environment and hermetically sealed against moisture invasion during storage or are packaged separately during storage. In one embodiment, the two calcium phosphate powders are packaged separately, wherein each powder is either packaged alone with no other components of the particulate composition of the invention or in admixture with one or more of the remaining components (e.g., the CSH powder).

In certain embodiments, the particulate composition of the invention will also include a plurality of non-porous β-TCP granules having a median particle size greater than the median particle size of the non-porous β-TCP powder. The non-porous β-TCP granules typically have a median particle size of about 75 to about 1,000 microns, more preferably about 100 to about 400 microns, and most preferably about 180 to about 240 microns. The granules serve to further reduce the resorption rate of the bone graft substitute cement and contribute to scaffold formation. The non-porous β-TCP granules are typically present at a concentration of up to about 20 weight percent, based on the total weight of the particulate composition, more preferably up to about 15 weight percent based on the total weight of the composition, and most preferably up to about 12 weight percent. In one preferred embodiment, the non-porous β-TCP granules are present at a concentration of about 8 to about 12 weight percent (e.g., about 10 weight percent). The non-porous β-TCP granules can provide a relatively inert third phase in the final cement that exhibits an even slower resorption rate than the brushite formed by reaction of the MCPM and the non-porous β-TCP powder. Thus, the presence of the granules can further alter the resorption profile of the resulting bone graft substitute cement.

Both the non-porous β-TCP granules and the non-porous β-TCP powder used in the present invention can be formed using a commercially available non-porous β-TCP powder as a starting material, such as non-porous β-TCP powder available from Plasma Biotal Ltd. (Derbyshire, UK). In one embodiment, the non-porous β-TCP components of the particulate composition are formed by first wet milling a commercially available non-porous β-TCP powder in a ball mill to a median particle size of less than 1.0 micron and then draining the resulting slurry through a strainer to remove the milling media. Thereafter, the solid cake of non-porous β-TCP can be separated from any remaining liquid components using any of a variety of techniques known in the art, such as centrifuging, gravity separation, filter pressing, evaporation, and the like. The dry cake is then processed through a series of sieves in order to produce two separate non-porous β-TCP components having different median particle sizes. The dried cake of non-porous β-TCP is typically milled either during or prior to sieving in order to fragment the cake. In one preferred embodiment, the system of sieves produces a non-porous β-TCP component having a particle size range of about 125 to about 355 microns in a green (i.e., unfired) state and another non-porous β-TCP component having a particle size range of about 75 to about 355 microns in a green state. Thereafter, the two non-porous β-TCP components are sintered, and thereby densified, by heat treatment in a furnace. In one embodiment, the furnace treatment involves heating the non-porous β-TCP powder components on an alumina plate at a temperature of about 1100-1200° C. for about three hours. It is typical to ramp the temperature up to the desired sintering temperature and ramp the temperature back down during the cooling period at a rate no greater than about 5-6° C. per minute.

Following the sintering process, the densified non-porous β-TCP granules having had a green state particle size of about 125 to about 355 microns can be used as the granule component of the particulate composition. The sintered non-porous β-TCP component having had a green (i.e., unfired) state particle size of about 75 to about 355 microns can be dry milled in a ball mill for approximately one to four hours in order to form the non-porous β-TCP powder having a median particle size of less than about 20 microns, which can then be used in the particulate composition as described above.

The porous β-TCP component comprises β-TCP particles that exhibit a relatively high degree of porosity as compared with the non-porous β-TCP component(s). Porous β-TCP can have various macrostructures and microstructures. The size of the particles can vary and can be, e.g., in granular or powder form. Also, the total surface area of the particles can vary and the shapes and sizes of the pores present within the β-TCP particles can also vary. In some embodiments, the porous β-TCP component comprises β-TCP particles having interconnected, multidirectional porosity. In some embodiments, the porous β-TCP component comprises β-TCP particles having a multiplicity of unconnected pores. Pore sizes (e.g., diameters) can range, for example, from about 100 microns to about 400 microns. Accordingly, in some embodiments, the porous β-TCP particles can be characterized as microporous, in some embodiments, the porous β-TCP can be characterized as macroporous, and in some embodiments, the porous β-TCP can be characterized as both microporous and macroporous. The total porosity can be at least about 50%, at least about 60%, or at least about 70%. In exemplary embodiments, the total porosity can range, e.g., from about 50% to about 90%, such as between about 60% and about 90% or between about 70% and about 90%. The total porosity values of a given material can be determined, e.g., by the measurement of the density by weight of a sample of the material. It is noted that the non-porous β-TCP described herein can, in some embodiments, be described as having a porosity of less than about 15% or less than about 10% as determined by scanning electron microscopy (SEM) images. It is noted that the porous β-TCP incorporated into the compositions described herein can, in certain embodiments, comprise some percentage of an alpha TCP phase. For example, in some embodiments, the porous β-TCP can comprise up to about 40% alpha-TCP.

In one exemplary embodiment, the porous β-TCP comprises CELLPLEX® TCP from Wright Medical Technology, Inc. (Tennessee, USA). See, for example, U.S. Pat. Nos. 6,136,029; 6,527,810; and 6,296,667, all to Johnson et al., which are all incorporated herein by reference in their entireties. Other commercially available porous β-TCP powders/granules include, but are not limited to: Conduit® TCP Granules (DePuy Synthes, Pa., USA); Ceros® TCP Granules (Thommen Medical, Inc., Switzerland); β-TCP Porous Granules (Cam BioCeramics, the Netherlands); Osprolife β-TCP Granules (Eurocoating, Italy); and BoneSigma™ Porous TCP (SigmaGraft, Inc., California, USA). Porous β-TCP can also be prepared as described, for example, in U.S. Pat. Nos. 7,390,498 and 6,949,251 to Dalal et al.; and U.S. Patent Application Publication Nos. 2006/0292200 to Delaney; and 2003/0180376 to Brevetto et al., which are incorporated herein by reference in their entireties.

The amount of porous β-TCP in the compositions described herein can vary. In certain embodiments, porous β-TCP is present at a concentration of up to about 20 weight percent, based on the total weight of the particulate composition and more preferably up to about 15 weight percent based on the total weight of the composition. In one preferred embodiment, the porous β-TCP is present at a concentration of about 5 to about 15 weight percent (e.g., about 10 weight percent).

The porous β-TCP portion of the particulate composition preferably has a bimodal particle size distribution characterized by a minority (i.e., less than about 50%), e.g., about 25% by weight, porous β-TCP having a smaller particle size and a majority (i.e., greater than about 50%), e.g., about 75%, porous β-TCP having a larger particle size. The particle sizes can vary; however, in a representative embodiment, the smaller particle size can be up to about 63 μm (i.e., about 0-63 μm) and the larger particle size can be greater than about 63 μm (e.g., from about 63 μm to about 250 μm). Accordingly, one specific bone substitute cement composition embodiment comprises porous β-TCP powder having a bimodal particle size distribution, wherein less than about 50% of the porous β-TCP powder has a particle size of between about 0 microns and about 63 microns and wherein greater than about 50% of the porous β-TCP powder has a particle size of between about 63 microns and about 250 microns.

The aqueous component that is mixed with the particulate composition of the invention is selected in order to provide the composition with a desired consistency and hardening or setting time. Typically, the aqueous solution is provided in an amount necessary to achieve a liquid to powder mass ratio (lip) of at least about 0.2, more preferably at least about 0.21, and most preferably at least about 0.23. A preferred lip ratio range is about 0.2 to about 0.3, more preferably about 0.2 to about 0.25. Examples of suitable aqueous components include water (e.g., sterile water) and solutions thereof, optionally including one or more additives selected from the group consisting of sodium chloride, potassium chloride, sodium sulfate, potassium sulfate, EDTA, ammonium sulfate, ammonium acetate, and sodium acetate. In one preferred embodiment, the aqueous mixing solution used is a saline solution or a phosphate buffered saline solution. An exemplary aqueous solution is 0.9% NaCl saline solution available from Baxter International (Deerfield, Ill.) and others.

In one embodiment, the aqueous solution further includes one or more organic or inorganic carboxylic acid-containing compounds (hereinafter carboxylic acids or carboxylic acid compounds) which may or may not contain a hydroxyl group on the alpha carbon, optionally titrated to a neutral pH using a suitable base (e.g., neutralized to a pH of about 6.5 to about 7.5 using an alkali metal base such as sodium hydroxide or potassium hydroxide), which can alter water demand, flowability, and/or viscosity of the bone graft substitute cement composition upon mixing. Exemplary carboxylic acids include glycolic acid and lactic acid. Preferred carboxylic acids have a single carboxylic acid group, from 1 to about 10 total carbon atoms (e.g., 1, 2, 3, 4, 5, 6, 7, 8, 9, or 10 carbon atoms including the carbonyl carbon), and 0-5 hydroxyl groups (e.g., 0, 1, 2, 3, 4, or 5) attached to the carbon chain. In one preferred embodiment, the mixing solution comprises glycolic acid, sodium hydroxide, and sodium chloride in water. Reference to the carboxylic acid compound herein encompasses both the free acid and salt forms.

It has been previously discovered, as detailed in U.S. Pat. No. 7,754,246 to Moseley et al., which is incorporated herein by reference, that the presence of the carboxylic acid component in the aqueous solution prior to gamma radiation sterilization can lead to inconsistent bone graft substitute cement properties, such as "drift" in cement setting time, due to degradation of the acid resulting from the radiation exposure. Thus, in one preferred embodiment, the carboxylic acid compound discussed above in connection with the aqueous mixing solution is packaged as a crystalline powder (e.g., in free acid or salt form) with the remaining particulate components of the kit, either in admixture with one or more other powder components or in a separate container, rather than in solution. Using the acid component in powder form avoids degradation of the acid upon sterilization of the composition with gamma radiation. Alternatively, the carboxylic acid component is added to the aqueous solution after the solution is sterilized by radiation so that the carboxylic acid is not exposed to sterilizing radiation while in solution.

In one embodiment, the carboxylic acid for use in the invention is neutralized to a pH of about 6.5 to about 7.5 in solution using, for example, an alkali metal base as noted above, and then isolated as a crystalline powder by evaporation of the solvent (e.g., water). The crystalline powder is typically isolated in a salt form, such as an alkali metal salt form (e.g., lithium, sodium, or potassium salts). Exemplary dry crystalline powders of a carboxylic acid, in salt form, for use in the invention include sodium glycolate, potassium glycolate, sodium lactate, and potassium lactate. The powdered carboxylic acid salt can be added to any of the other powder ingredients that together form the particulate portion of the bone graft substitute cement, such as the CSH component or either of the calcium phosphate components. However, in certain embodiments, the powdered carboxylic acid is stored in a separate container so that it can be reconstituted with the aqueous solution prior to mixing the solution with the remaining particulate components of the composition.

Although brushite-forming components are preferred in the inventive compositions of the invention, certain embodiments of the invention do not include one or both brushite-forming components. For example, in certain embodiment of the invention, the composition includes CSH as described herein (in any of the amounts noted herein), a porous β-TCP component as described herein (in any of the amounts noted herein), and a porous β-TCP granule component as described herein (in any of the amounts noted herein). Such embodiments can be supplemented with one of the brushite-forming components, such as the β-TCP powder or the MCPM powder as described herein (in any of the amounts noted herein).

The bone graft substitute cement of the invention can further include other additives known in the art. The additives can be added as a solid or liquid to either the particulate composition of the invention or the aqueous mixing solution. One example of an additive for the calcium sulfate composition is a plasticizer designed to alter the consistency and setting time of the composition. Such a plasticizing ingredient can retard the setting of calcium sulfate hemihydrate pastes, thereby increasing the time it takes for the composition to set following mixing with an aqueous solution. Exemplary plasticizers include glycerol and other polyols, vinyl alcohol, stearic acid, hyaluronic acid, cellulose derivatives and mixtures thereof. Alkyl celluloses are particularly preferred as the plasticizer ingredient. Exemplary alkyl celluloses include methylhydroxypropylcellulose, methylcellulose, ethylcellulose, hydroxyethylcellulose, hydroxypropylcellulose, hydroxypropylmethylcellulose, carboxymethylcellulose, cellulose acetate butyrate, and mixtures or salts thereof.

Exemplary additives also include biologically active agents. As used herein, the term "biologically active agent" is directed to any agent, drug, compound, composition of matter or mixture that provides some pharmacologic effect that can be demonstrated in vivo or in vitro. Examples of biologically active agents include, but are not limited to, peptides, proteins, enzymes, small molecule drugs, dyes, lipids, nucleosides, oligonucleotides, polynucleotides, nucleic acids, cells, viruses, liposomes, microparticles, and micelles. It includes agents that produce a localized or systemic effect in a patient.

Particularly preferred classes of biologically active agents include osteoinductive or osteoconductive materials, antibiotics, chemotherapeutic agents, pesticides (e.g., antifungal agents and antiparasitic agents), antivirals, anti-inflammatory agents, and analgesics. Exemplary antibiotics include ciprofloxacin, tetracycline, oxytetracycline, chlorotetracycline, cephalosporins, aminoglycocides (e.g., tobramycin, kanamycin, neomycin, erithromycin, vancomycin, gentamycin, and streptomycin), bacitracin, rifampicin, N-dimethylrifampicin, chloromycetin, and derivatives thereof. Exemplary chemotherapeutic agents include cis-platinum, 5-fluorouracil (5-FU), taxol and/or taxotere, ifosfamide, methotrexate, and doxorubicin hydrochloride. Exemplary analgesics include lidocaine hydrochloride, bipivacaine and non-steroidal anti-inflammatory drugs such as ketorolac tromethamine. Exemplary antivirals include gangcyclovir, zidovudine, amantidine, vidarabine, ribaravin, trifluridine, acyclovir, dideoxyuridine, antibodies to viral components or gene products, cytokines, and interleukins. An exemplary antiparasitic agent is pentamidine. Exemplary anti-inflammatory agents include α-1-anti-trypsin and α-1-antichymotrypsin.

Useful antifungal agents include diflucan, ketaconizole, nystatin, griseofulvin, mycostatin, miconazole and its derivatives as described in U.S. Pat. No. 3,717,655, the entire teachings of which are incorporated herein by reference; bisdiguanides such as chlorhexidine; and more particularly quaternary ammonium compounds such as domiphen bromide, domiphen chloride, domiphen fluoride, benzalkonium chloride, cetyl pyridinium chloride, dequalinium chloride, the cis isomer of 1-(3-chlorallyl)-3,5,7-triaza-1-azoniaadamantane chloride (available commercially from the Dow Chemical Company under the trademark Dowicil 200) and its analogues as described in U.S. Pat. No. 3,228,828, the entire teachings of which are incorporated herein by reference, cetyl trimethyl ammonium bromide as well as benzethonium chloride and methylbenzethonium chloride such as described in U.S. Pat. Nos. 2,170,111; 2,115,250; and 2,229,024, the entire teachings of which are incorporated herein by reference; the carbanilides and salicylanilides such 3,4,4'-trichlorocarbanilide, and 3,4,5-tribromosalicylanilide; the hydroxydiphenyls such as dichlorophene, tetrachlorophene, hexachlorophene, and 2,4,4'-trichloro-2'-hydroxydiphenylether; and organometallic and halogen antiseptics such as zinc pyrithione, silver sulfadiazone, silver uracil, iodine, and the iodophores derived from non-ionic surface active agents such as described in U.S. Pat. Nos. 2,710,277 and 2,977,315, the entire teachings of which are incorporated herein by reference, and from polyvinylpyrrolidone such as described in U.S. Pat. Nos. 2,706,701, 2,826,532 and 2,900,305, the entire teachings of which are incorporated herein by reference.

As used herein, the term "growth factors" encompasses any cellular product that modulates the growth or differentiation of other cells, particularly connective tissue progenitor cells. The growth factors that may be used in accordance with the present invention include, but are not limited to, fibroblast growth factors (e.g., FGF-1, FGF-2, FGF-4); platelet-derived growth factor (PDGF) including PDGF-AB, PDGF-BB and PDGF-AA; bone morphogenic proteins (BMPs) such as any of BMP-1 to BMP-18; osteogenic proteins (e.g., OP-1, OP-2, or OP-3); transforming growth factor-α-, transforming growth factor-β (e.g., β1, β2, or β3); LIM mineralization proteins (LMPs); osteoid-inducing factor (OIF); angiogenin(s); endothelins; growth differentiation factors (GDF's); ADMP-1; endothelins; hepatocyte growth factor and keratinocyte growth factor; osteogenin (bone morphogenetic protein-3); heparin-binding growth factors (HBGFs) such as HBGF-1 and HBGF-2; the hedgehog family of proteins including indian, sonic, and desert hedgehog; interleukins (IL) including IL-1 thru -6; colony-stimulating factors (CSF) including CSF-1, G-CSF, and GM-CSF; epithelial growth factors (EGFs); and insulin-like growth factors (e.g., IGF-I and -II); demineralized bone matrix (DBM); cytokines; osteopontin; and osteonectin, including any isoforms of the above proteins. Particulate DBM is a preferred osteoinductive additive.

The biologically active agent may also be an antibody. Suitable antibodies, include by way of example, STRO-1, SH-2, SH-3, SH-4, SB-10, SB-20, and antibodies to alkaline phosphatase. Such antibodies are described in Haynesworth et al., Bone (1992), 13:69-80; Bruder, S et al., Trans Ortho Res Soc (1996), 21:574; Haynesworth, S. E., et al., Bone (1992), 13:69-80; Stewart, K., et al, J Bone Miner Res (1996), 11(Suppl.):S142; Flemming J. E., et al., in "Embryonic Human Skin. Developmental Dynamics," 212:119-132, (1998); and Bruder S. P. et al., Bone (1997), 21(3): 225-235, the entire teachings of which are incorporated herein by reference.

Other examples of biologically active agents include bone marrow aspirate, platelet concentrate, blood, allograft bone, cancellous bone chips, synthetically derived or naturally derived chips of minerals such as calcium phosphate or calcium carbonate, mesenchymal stem cells, and chunks, shards, and/or pellets of calcium sulfate.

A bone graft substitute cement according to the invention can be formed by mixing the particulate composition with the aqueous solution using manual or mechanical mixing techniques and apparatus known in the art. It is preferred to mix the components of the cement at atmospheric pressure or below (e.g., under vacuum) and at a temperature that will not result in freezing of the aqueous component of the mixture or significant evaporation. Following mixing, the homogenous composition typically has a paste-like consistency, although the viscosity and flowability of the mixture can vary depending on the additives therein. The bone graft substitute cement material can be transferred to a delivery device, such as a syringe, and injected into a target site, for example, to fill in cracks or voids of a bone defect. In some embodiments, the material can be injected through an 8- to 16-gauge needle up to, for example, 10 cm long.

The bone graft substitute cements of the invention will generally set, as defined by the Vicat needle drop test set forth below, in about 3 to about 25 minutes, more preferably about 5 to about 15 minutes (e.g., between about 5 and about 12 minutes). The bone graft substitute cement material of the invention will typically reach a hardness comparable to or greater than bone within about 8 to about 60 minutes or about 10 to about 60 minutes (e.g., having a Gillmore set time of between about 8 and about 30 minutes or about 12 to about 30 minutes, more preferably between about 12 and about 20 minutes, e.g., between about 14 and about 17 minutes). Setting of the material can occur in a variety of environments, including air, water, in vivo, and under any number of in vitro conditions. It is noted that the presence of certain biologically active agents in the material may retard the set time of the material to some extent, as described in greater detail below.

Although not intended to be limited by theory, it is believed that, in certain embodiments, one or more of the specific powder component ratios, the use of porous β-TCP, and/or the use of a mixing solution comprising sodium chloride in the glycolic acid solution contribute, at least in part, to the enhanced setting properties of the bone graft substitute here. By "enhanced setting properties" is meant that such compositions set in the presence of biologically active agents and set more quickly (with shorter Vicat and Gillmore set times) than similar, commercially available compositions (e.g., Pro-Dense®, Wright Medical Technology, Inc., Tennessee, USA).

In certain embodiments, the compositions described herein are uniquely capable of achieving a relatively fast set time even in the presence of various biologically active agents (e.g., including but not limited to, in the presence of bone marrow aspirate or in the presence of platelet derived growth factors). Interestingly, compositions described in the present disclosure can exhibit improved properties as compared with a commercially available composition (Pro-Dense®, Wright Medical Technology, Inc.) prepared as described in U.S. Pat. No. 7,754,246 to Moseley et al., which is incorporated herein by reference in its entirety. When biologically active agents are incorporated in the bone graft substitute cements described herein, the cements may exhibit a slight delay in setting as compared with identical bone graft substitute cements that are free of biologically active agents. However, the compositions described herein are uniquely capable of hard setting even in the presence of various such biologically active agents. For example, in certain embodiments, compositions as described herein, further comprising one or more biologically active agents can exhibit a Vicat set time of about 25 minutes or less, about 20 minutes or less, about 15 minutes or less, or about 10 minutes or less (e.g., between about 7 and about 15 minutes or between about 10 and about 15 minutes). In certain embodiments, compositions as described herein, further comprising one or more biologically active agents can exhibit a Gillmore set time of about 35 minutes or less, about 30 minutes or less, about 25 minutes or less or about 20 minutes or less (e.g., between about 10 and about 20 minutes or between about 15 and about 20 minutes).

The hardened bone graft substitute cement preferably exhibits certain mechanical strength properties, particularly as characterized by diametral tensile strength and compressive strength. Preferred embodiments of the cement exhibit a diametral tensile strength of at least about 4 MPa after curing for one hour in ambient air following mixing of the particulate composition with an aqueous solution, more preferably a diametral tensile strength of at least about 5 MPa, most preferably at least about 6 MPa. Further, preferred embodiments of the bone graft substitute cement exhibit a diametral tensile strength of at least about 8 MPa after curing for 24 hours in ambient air following mixing of the particulate composition with an aqueous solution, more preferably a diametral tensile strength of at least about 9 MPa after curing for 24 hours, and most preferably at least about 10 MPa.

The bone graft substitute cement of the invention typically exhibits a dissolution rate that is significantly slower than a comparable bone graft substitute cement made substantially entirely of calcium sulfate. In certain preferred embodiments, the cement of the invention exhibits an average dissolution rate, expressed as an average percentage of weight loss per day, that is at least about 25% lower than the average dissolution rate of a cement formed using a particulate composition consisting of calcium sulfate, the average dissolution rate measured by immersion of a 4.8 mm OD pellet having a length of 3.3 mm in distilled water at 37° C. as described in greater detail below. More preferably, the bone graft substitute cement of the invention has an average dissolution rate that is at least about 30% lower than a calcium sulfate cement, most preferably at least about 35% lower, and in some embodiments, as much as 40% lower or more. A preferred range of dissolution, expressed as an average percentage of weight loss per day measured using the test procedure set forth below, is about 5% to about 15%, more preferably about 7% to about 13%. Average dissolution rates stated are determined by linear regression of % weight loss per day using data from days 0, 1, 2, 3, and 4 determined using the procedure set forth below.

The present invention also provides a bone graft substitute kit comprising the particulate composition of the invention. Typically, the kit comprises one or more containers enclosing the particulate composition as described above and a separate container enclosing a sterile aqueous solution. The kit will typically contain a written instruction set describing a method of using the kit. In addition, the bone-graft substitute kit of the invention will preferably comprise an apparatus for mixing the particulate composition with the aqueous solution in order to form the bone graft cement, such as a vacuum mixing apparatus. Additionally, the kit will typically include a device for delivering the bone graft cement to the site of the bone defect, such as an injection device (e.g., a needle and syringe).

As noted previously, in certain embodiments, the kit of the invention will separate the two calcium phosphate powder components into different containers to avoid reaction during storage. There are a number of packaging configurations that can accomplish this goal. For example, in one embodiment, the kit includes one container for CSH powder, one container for β-TCP powder, and one container for MCPM powder. In another embodiment, the kit includes two containers for the particulate composition, one including β-TCP powder and a portion of the CSH component and a second containing MCPM powder and a portion of the CSH component. In yet another embodiment, the MCPM powder is packaged in a separate container by itself, and the β-TCP powder and the CSH powder are packaged together. In a still further embodiment, the β-TCP powder is packaged in a separate container by itself, and the MCPM powder and the CSH powder are packaged together. In any of the above embodiments, any of the powder containers can further include the crystalline powder of the carboxylic acid salt component and/or the β-TCP granules, or those components could be packaged separately in their own containers. When present, the accelerator adapted to accelerate conversion of CSH to CSD is typically in admixture with the CSH powder. In one preferred embodiment, the kit comprises one container enclosing the MCPM powder, and a second container enclosing the remaining particulate ingredients in admixture, such as one or more of the CSH powder, the CSH accelerator, the β-TCP powder, the β-TCP granules, and the carboxylic acid crystalline powder.

In certain embodiments, a dual syringe mixing system can be incorporated in the kit. The dual syringe system may afford an alternative means for separating the components of the kit as noted above. For example, in one embodiment, one syringe can contain the MCPM component and a second syringe can contain the remaining powder components of the bone graft substitute composition. The liquid component can be provided, for example, in a vial, such as a crimp-top vial, which can be attached to the end of one syringe to draw the liquid into either the MCPM component or the remaining powder components of the composition. The two syringes can then be connected (e.g., with a syringe connector), and the liquid material can be passed back and forth between the two syringes to afford complete mixing of the components. For injection, the mixture can be drawn into one of the syringes, the syringe connector and other syringe can be removed, and a needle can be applied to the end of the mixture-containing syringe.

FIG. 4 illustrates one embodiment of a bone graft substitute kit 100 suitable for use in the present invention, and FIG. 5 illustrates a method of preparing a bone graft substitute composition using the kit of FIG. 4. As shown in FIG. 4, the kit 100 includes two syringes containing particulate material, a first syringe 110 labelled "Part A" containing a majority of the powder components of the kit and a second syringe 120 labelled "Part B" containing a minor portion of the powder components of the kit. Although the contents of each syringe can vary, in one embodiment, the Part A syringe includes all powder/granular components except the MCPM component and the Part B syringe contains the MCPM component. The kit 100 also contains a liquid-containing vial 130 containing the mixing diluent solution, which can be, for example, a saline solution containing glycolic acid. The vial 130 will typically include a lid comprising a pierceable septum. The sizes of the syringes, 110 and 120, as well as the vial 130 will depend on the desired amount of bone graft substitute material to be made, and will typically vary in size as needed to produce bone graft substitute compositions in amounts ranging from about 1 cc to 10 cc (e.g., about 2 cc to about 4 cc).

The illustrated kit 100 also contains a syringe connector 140 and a vial adaptor 150. The syringe connector 140 typically includes a connector at each end for facilitating connection, such as threaded connection, of the connector to a syringe and a passageway adapted to allow fluid to pass from one connected syringe to the other. The vial adaptor 150 typically includes a connector for connecting to a syringe, such as through threaded engagement, a passageway adapted to allow fluid to pass from a vial into the syringe, and a spike adapted for piercing a septum of a vial. Finally, the kit 100 may contain one or more, and preferably multiple, needles for delivery of the bone graft substitute composition to the bone site in need thereof. The illustrated kit 100 contains two needles, 160 and 170, which are shown as advantageously being of the Jamshidi type, the two needles differing in size (e.g., differing in length and/or gauge). As shown, one exemplary kit 100 contains a 11-gauge Jamshidi needle 160 of a first length and a 16-gauge Jamshidi needle 170 of a second, shorter length. Other sizes or needle types could be used without departing from the invention. The kit will also typically contain a written instruction set, such as a set of instructions outlining the basic method set forth in FIG. 5 and explained herein.

As set forth in FIG. 5, one method of using the kit 100 of FIG. 4 involves the step 200 of attaching the vial adaptor 150 to the Part A syringe 110 (after removing any cap present on the syringe). The vial adaptor 150 can join the syringe 110 in any manner, such as through threaded engagement. Thereafter, the method can include the step 210 of attaching the mixing diluent vial 130 to the vial adaptor 150, which will result in the spike (not shown) of the vial adaptor piercing the septum of the vial. Advantageously, one can draw back the Part A syringe 110 to draw air into the syringe before attaching the vial 130. The contents of the vial 130 can then be withdrawn into the Part A syringe 110 in step 220, which can be preceded by injection of the air optionally drawn into the syringe into the vial. Multiple injection/withdrawal steps may be required to withdraw all liquid from the vial 130. Thereafter, the vial 130 and vial adaptor 150 can be removed from the syringe 110 and the syringe connector 140 can be attached to the Part B syringe 120 in step 230. Thereafter, the two syringes, 110 and 120, can be attached together via the syringe connector 140 in step 240. Application of an alternating plunging action to the two syringes in step 250 will enable the materials in the two syringes to mix well. In certain embodiments, the alternating plunging of the syringes should occur at least about 20 times, such as at least about 30 or at least about 40 times. To avoid loss of injectability of the material, it is advantageous to inject the bone graft substitute material within about 6 minutes (such as within about 5 minutes or within about 3 minutes) of the time the liquid is first added to the powder material.

Once the materials are thoroughly mixed, the two syringes can be decoupled in step 260 (with all bone graft substitute material in one syringe) and a delivery needle (e.g., needle 160 or 170) can be attached to the syringe containing the bone graft material. Finally, in step 270, the bone graft substitute material is delivered to the desired bone site using the syringe/needle device.

The particular composition and the sterile aqueous solution will typically be sterilized by irradiation prior to packaging in the kit. In one preferred embodiment, the powdered form of the carboxylic acid is packaged separately so that it can be reconstituted in the aqueous solution, if desired, prior to mixing the solution with the remaining particulate components. However, as noted previously, the aqueous solution of the kit may also contain the carboxylic acid component in solution form if the carboxylic acid is added after radiation sterilization of the aqueous component of the kit.

It can be important to utilize all of the aqueous solution packaged in the kit in order to ensure that consistent setting times are achieved. In one embodiment, the aqueous solution is packaged in a highly hydrophobic container, such as a glass syringe or other glass container, which is less prone to retention of residual solution in amounts that will cause changes in the performance characteristics of the bone graft substitute cement. When mixing with a biologically active agent, it may in some embodiments be beneficial to use a specified ratio of aqueous solution to biologically active agent. For example, in one specific embodiment, desirable results are achieved using bone marrow aspirate in a ratio of 60:40 solution to bone marrow aspirate to achieve an injectable, fast-setting material.

The present invention also provides a method for treating a bone defect. The method of the invention involves applying a bone graft substitute cement as described above to the site of the bone defect. The bone graft substitute cement can be applied in flowable farm following mixing of the particulate composition with the aqueous solution. For example, methods of application include, but are not limited to, applying the cement through an injection device or digitally packing the cement, prior to setting of the composition. Alternatively, the bone graft substitute cement can be used in a precast hardened form, wherein the cement is provided in predetermined shapes such as pellets, granules, wedges, blocks, or disks, or used in the form of randomly-shaped shards created by mechanically breaking a cement mass into smaller pieces. In a further embodiment, the clinician can form the bone graft cement mixture and manually mold the mixture into a desired shape, such as the shape needed to fill a particular bone defect, prior to application.

In another embodiment, the bone graft substitute cement of the invention can be incorporated into an orthopedic implant, such as any of the various devices adapted for joint replacement. The bone graft substitute cement is typically incorporated into such devices as an outer coating or as a filling material within the pores of a porous outer component of the device. In this embodiment, the bone graft substitute cement facilitates bone in-growth in the area surrounding the implanted device. Exemplary orthopedic implants include knee replacement devices (e.g., constrained or non-constrained knee implant devices, hinged knee devices, metallic plateau knee devices, and patellar devices), hip replacement devices (e.g., acetabular components and femoral components), elbow replacement devices (e.g., constrained, semi-constrained, and non-constrained devices), upper femoral devices, upper humeral devices, wrist replacement devices (e.g., semi-constrained 2- and 3-part articulation devices), shoulder devices, passive tendon devices, spinal devices (e.g., thoracolumbar spinal fixation devices, cervical spinal fixation devices, and spinal fusion cages), finger/toe devices, and diaphysis devices.

The present invention will be further illustrated by the following non-limiting examples.

EXPERIMENTAL

Example 1

One exemplary embodiment of the presently disclosed composition is provided as follows below in Table 1.

TABLE 1

Inventive Composition A

| Component | Percent by weight | Particle size range |
|---|---|---|
| Calcium sulfate hemihydrate | 71.90% | 5 μm-10 μm |
| Accelerator | 0.10% | ≤595 μm |
| Non-porous β-TCP granules | 10% | 180 μm-240 μm |
| Porous β-TCP granules (0-63 μm) | 2.50% | 0 μm-63 μm |
| Porous β-TCP granules (63-250 μm) | 7.50% | 63 μm-250 μm |
| Non-porous β-TCP powder | 4.41% | 13.3 μm-15.7 μm |
| MCPM | 3.59% | ≤350 μm |
| Glycolic acid in saline solution | 0.25 l/p* | |

*liquid to powder mass ratio

The Inventive Composition A powder components, excluding MCPM, are weighed out to the appropriate amount and mixed in a V-shape blender for a minimum of ten minutes. The MCPM and glycolic acid components are weighed out and set aside. After mixing, the powder components are added to a mixer. The MCPM is then added, and the powder and MCPM are stirred to combine. The glycolic acid/saline solution is added, and a timer is started. The mixture is mixed at a rate of 50 rotations per 30 seconds. The resultant paste is then typically transferred to a syringe for immediate use.

For use within a dual syringe system as described herein, the blended powder components are located in one syringe and the MCPM is located in the second syringe. The glycolic acid/saline solution (present, e.g., in a vial having a puncturable septum) is pulled into the blended powder-containing syringe via suction. This syringe is then connected to the MCPM syringe via a connector, and the mixture is mixed 30 times between the syringes.

A comparative composition (commercially available Pro-Dense® material, Wright Medical Technology, Inc., Tennessee, USA) is prepared as described in U.S. Pat. No. 7,754,246 to Moseley et al., which is incorporated herein by reference, with specific components and amounts as noted below in Table 2.

TABLE 2

Comparative Composition

| Component | Percent by weight | Particle Size Range |
|---|---|---|
| Calcium sulfate hemihydrate | 74.906% | 5 μm-10 μm |
| Accelerator | 0.094% | ≤595 μm |
| Non-porous β-TCP granules | 10.000% | 180 μm-240 μm |
| Non-porous β-TCP power | 8.30% | 13.3 μm-15.7 μm |
| MCPM | 6.700% | ≤350 μm |
| Glycolic acid solution | 0.25 l/p | |

Work Times/Set Times:

Inventive Composition A (Table 1) is compared against the Comparative Composition (Table 2, which is a standard, commercially available Pro-Dense® composition). Inventive Composition A exhibits a work time (injection/delivery time) of 3-5 minutes, a Vicat set time (point at which the composition is no longer deformable without fracture) of 8-12 minutes, and Gillmore set time (point at which a rock hard set is achieved) of 14-17 minutes. The Comparative Composition exhibits a work time of 3-5 minutes, a Vicat set time of 14-19 minutes, and a Gillmore set time of 30+ minutes.

Data for set times of both Inventive Composition A and the Comparative Composition in the presence of various biologically active agents are also provided. Table 3 illustrates set times for trials with both compositions, incorporating a sodium acetate buffer and/or recombinant human platelet derived growth factor (rhPDGF-BB) in the buffer. As noted in the table, the Inventive Composition exhibited lower set times as compared to the Comparative Composition in the presence of certain biologically active agents.

TABLE 3

Set Time Data for Inventive Composition A and Comparative Composition in the presence of biologically active agents

| Trial | Graft material | Graft powder (g) | Graft diluent (g) | Sodium acetate 20 mM (g) ("buffer") | rhPDGF-BB@ 0.3 mg/mL in buffer (g) | Vicat set time (min) | Gillmore set time (min) |
|---|---|---|---|---|---|---|---|
| 1 | Comparative Composition with sodium acetate buffer | 22.0 | 2.2 | 3.0 | | 23:30 | |
| 2 | Comparative Composition with rhPDGF-BB | 22.0 | 2.2 | | 3.0 | 23:30 | 40:00-43:00 |

TABLE 3-continued

Set Time Data for Inventive Composition A and Comparative Composition in the presence of biologically active agents

| Trial | Graft material | Graft powder (g) | Graft diluent (g) | Sodium acetate 20 mM (g) ("buffer") | rhPDGF-BB@ 0.3 mg/mL in buffer (g) | Vicat set time (min) | Gillmore set time (min) |
|---|---|---|---|---|---|---|---|
| 3 | Inventive Composition A with rhPDGF-BB | 25.0 | 3.4 | | 3.0 | 15:00 | ≤17:45 |
| 4 | Inventive Composition A | 25.0 | 6.4 | | | 13:00 | 16:50 |
| 5 | Inventive Composition A with sodium acetate buffer | 25.0 | 3.4 | 3.0 | | 12:30 | 14:00 |

Tables 4 and 5 illustrate set times for trials with the Comparative Composition and various inventive compositions and other comparative compositions incorporating antibiotics Tobramycin (Table 4) or Vancomycin (Table 5). Bead set times, as shown in Tables 4 and 5, are determined by preparing the bone graft pastes (with or without antibiotics); and pressing the pastes into bead molds to form beads of uniform size. "Bead set time" refers to the amount of time required for the beads to remain in the mold so that they will not deform once the bead mold is removed.

TABLE 4

Set Time Data for various compositions in the presence and absence of Tobramycin

| | No antibiotics | | | Tobramycin | | |
|---|---|---|---|---|---|---|
| Graft material | Vicat Set Time (min) | Gillmore Set Time (min) | Bead Set Time (min) | Vicat Set Time (min) | Gillmore Set Time (min) | Bead Set Time (min) |
| Comparative Composition | 19.5 | 47 | 47 | 38 | 54 | 46 |
| Composition A1 (75% CSH, 25% non-porous TCP granules) | <10.5 | <10.5 | <10.5 | 11.5 | 17 | 15 |
| Composition A2 (85% CSH, 10% non-porous TCP granules, 5% brushite (equimolar TCP powder and MCPM)) | 13.25 | 17 | 17 | 13 | 15 | 15 |
| Composition A2 Deriv. (82% CSH, 10% non-porous TCP granules, 8% brushite (equimolar TCP powder and MCPM)) | 17 | 21 | 21 | 12 | 16 | 19 |
| Inventive Composition A3 (75% CSH, 10% non-porous TCP granules, 15% porous TCP granules (<1 mm)) | 9.5 | 11.5 | 11.5 | 10.5 | 16 | 16 |
| Inventive Composition A4 (75% CSH, 15% non-porous TCP granules, 10% porous TCP granules (<1 mm)) | 7 | 9.5 | 8.5 | 12.5 | 23 | 17 |
| Inventive Composition A5 (75% CSH, 14% non-porous TCP granules, 6.6% porous TCP granules (<1 mm), 4.4% MCPM | 16 | 19 | 19 | 13 | 21 | 21 |
| Inventive Composition A6 (75% CSH, 10% non-porous TCP granules, 10% porous TCP granules (<1 mm), 5% brushite (equimolar TCP powder and MCPM) | 11 | 14.5 | 14.5 | 15 | 19 | 17 |
| Inventive Composition A (Table 1) | 13.5 | 16.5 | 16.5 | 23 | 29 | 31 |

TABLE 5

Set Time Data for various compositions in the presence and absence of Vancomycin

| Graft material | No antibiotics | | | Vancomycin | | |
| --- | --- | --- | --- | --- | --- | --- |
| | Vicat Set Time (min) | Gillmore Set Time (min) | Bead Set Time (min) | Vicat Set Time (min) | Gillmore Set Time (min) | Bead Set Time (min) |
| Comparative Composition | 19.5 | 47 | 47 | 25 | 63 | ~60 |
| Composition A1 (75% CSH, 25% non-porous TCP granules) | <10.5 | <10.5 | <10.5 | 9.5 | 14 | 14 |
| Composition A2 (85% CSH, 10% non-porous TCP granules, 5% brushite (equimolar TCP powder and MCPM)) | 13.25 | 17 | 17 | 20.8 | 24.2 | 23.5 |
| Composition A2 Deriv. (82% CSH, 10% non-porous TCP granules, 8% brushite (equimolar TCP powder and MCPM)) | 17 | 21 | 21 | 24.0 | 28.0 | 28 |
| Inventive Composition A3 (75% CSH, 10% non-porous TCP granules, 15% porous TCP granules (<1 mm)) | 9.5 | 11.5 | 11.5 | 12.5 | 17 | 17 |
| Inventive Composition A4 (75% CSH, 15% non-porous TCP granules, 10% porous TCP granules (<1 mm) | 7 | 9.5 | 8.5 | 12.75 | 19 | 19 |
| Inventive Composition A5 (75% CSH, 14% non-porous TCP granules, 6.6% porous TCP granules (<1 mm), 4.4% MCPM | 16 | 19 | 19 | 27.25 | 32.5 | 32.5 |
| Inventive Composition A6 (75% CSH, 10% non-porous TCP granules, 10% porous TCP granules (<1 mm), 5% brushite (equimolar TCP powder and MCPM) | 11 | 14.5 | 14.5 | 16.75 | 19 | 20 |
| Inventive Composition A (Table 1) | 13.5 | 16.5 | 16.5 | 17.5 | 21.5 | 20 |

As noted in Tables 4 and 5, all of the tested compositions exhibited an improvement in set time in the presence of antibiotics as compared to the Comparative Composition (i.e., PRO-DENSE® composition). However, some of the tested compositions, such as Composition A1, Composition A2, and Composition A2 Deriv., did not compare as favorably with PRO-DENSE® composition in other properties, such as strength, ejection force, or dissolution rate.

The inventive compositions comprising the porous granule component were particularly advantageous compositions with respect to a number of physical properties, with Inventive Compositions A, A5, and A6 providing the best overall profile of properties such as set time and diametral tensile strength (DTS).

Set Times:

Vicat set times described herein are measured using a Vicat needle that is 1 mm in diameter, 5 cm long, and which possesses a total weight of 300 g, all per ASTM C-472, which is incorporated by reference herein in its entirety. The sample being tested should be mixed in a manner that a homogeneous, flowable paste is created. The sample size for the Vicat needle drop test is about 3 cc to about 5 cc of material tapped down to a cake in an approximately 20 mL polyethylene cup; the sample is handled such that no agitation is inflicted upon the material 1 minute after the aqueous solution contacts the particulate composition other than the dropping and removal of the Vicat needle. The cup is of such dimensions that the cake is a short, flat cylinder measuring about ¼" to about ⅜" in height.

Set time according to the Vicat needle drop test is defined as the amount of time elapsed between the time the aqueous solution contacts the particulate composition and the time the Vicat needle will not pass through 50% of the height of a cement sample upon being dropped from the upper surface of the sample. The needle is allowed to fall under its own weight, under gravity alone, through a line perpendicular to the top and bottom, flat faces of the cylinder-shaped sample cake. The needle is dropped every 30 seconds after the first drop. The needle shall not be dropped more than 6 times during the duration of the test. If after the 6$^{th}$ drop the needle continues to pass through more that 50% of the height of the sample, the test must be repeated with fresh material; a new, clean cup; and a clean Vicat needle free of debris, especially that which is left behind from previous tests. Cups, mixing equipment, and material transfer equipment should not be reused. All materials and equipment used during testing should be between 21-27° C. and exposed to an environment with a relative humidity between 20-50%.

Gillmore set times as described herein are tested based on ASTM standard C266-08: Standard Test Method for Time of Setting of Hydraulic-Cement Paste by Gillmore Needles. Similarly to Vicat set time determination, a sample of material is prepared and placed into a small cup. After determining the Vicat set time of the sample, a 453.6 gram weight with a 1.06 mm diameter needle is lightly placed onto the surface of the sample. The testing is continued at 1 minute intervals until there is no appreciable indentation left by the needle on the surface of the sample.

Work time as described herein is a description of the amount of time from immediately after the fluid component is added to the powder component until the material can no longer be reasonably ejected from a syringe/needle. Accordingly, "work time" as used herein includes the mixing time, the time to transfer the material to a syringe and the time it takes to complete ejection the material to its final placement.

Ejection Force:

The ejection force (measured 3 minutes after mixing the solution and powder components of the compositions) for both the Inventive Composition A (indicated as "FastSet") and the Comparative Composition (indicated as "PRO-DENSE®") is provided in FIG. 1. The left-most bar on the graph represents Inventive Composition A, injected through an 11 gauge needle, the middle bar represents Inventive Composition A, injected through an 8 gauge needle, and the right-most bar on the graph represents the Comparative Composition, injected through an 11-gauge needle. The graph indicates that Inventive Composition A has acceptable values of ejection force through 8-gauge and 11-gauge needles.

Diametral Tensile Strength:

The diametral tensile strength (DTS) of the Inventive Composition A is tested and compared against the DTS of the Comparative Composition in FIG. 2. As shown in FIG. 2, the DTS, after 24 hours of cure time, is somewhat higher for Inventive Composition A (indicated as "FastSet") than for the Comparative Composition (indicated as "PRO-DENSE®"). The difference in DTS between the Comparative Composition and Inventive Composition A at 24 hours is statistically significant.

Diametral tensile strength is determined through the following test methodology. A 1" cube of 10 lb/ft$^3$ closed-cell polyurethane foam (available as Last-A-Foam® from General Plastics Manufacturing Company, Tacoma, Wash.) with an approximately ⅝ in. (15.8 mm) outer diameter cylindrical void and notches for side removal is used as the specimen mold. The approximately ⅝ in. outer diameter cylindrical void is created by drilling perpendicularly through opposite faces of the cube in one depression of a drill press utilizing a ⅝ in. drill bit. The void runs the entire length of the cube and is centered such that both opposite, drilled faces share the same center as the circular voids created in them from the drilling. Two opposite sides from the remaining four full sides are designated to become the open sides of the final specimen; these sides will be removed via the notches. These sides are notched, two notches per side, in a manner such that they can be removed immediately prior to testing and not affect the sample integrity. The notches run the entire length of the cube and are separated in a manner that upon removal, >50% of the height of the specimen is exposed. Commonly the notches are created using an upright band saw. Further details regarding exemplary tensile test molds are provided in U.S. Pat. No. 7,754,246 to Moseley et al. and U.S. Patent Application Publication No. 2007/0059281 to Carroll et al., which are incorporated herein by reference.

The material to be tested is mixed to a homogeneous paste and loaded into a device suitable for injection of the paste into the 16 mm outer diameter cylindrical void. Commonly, a 30 cc syringe with a 1 cm opening is used for this. The mold is held by hand using the thumb and middle finger positioned on the opposite, notched sides. The index finger of the hand used to hold the mold is positioned over one of the circular openings. The material is then injected into the void from the opposite side of the void from the index finger; the entire face of the syringe exhibiting the 1 cm opening is lightly pushed up against the circular opening of the mold. Upon injection of the material into the mold, pressure will be felt on the index finger covering the back opening from the ejected material. The index finger is slowly removed while filling continues, allowing the paste to flow out of the rear of the mold in an extrusion with the same 16 mm outer diameter as the void. The syringe is slowly backed out from the front opening while back filling of paste is performed through further ejection from the syringe until the entire void is filled and excess material is located outside the dimensions of the original cube of foam. The front and rear sides of the specimen are wiped smooth, flush with the front and rear sides of the mold using a spatula. All specimens to be tested should be made within 2 minutes from the start of mixing, defined by the aqueous solution coming into contact with the particulate composition.

The specimens are allowed to cure horizontally in air in the mold with the front and rear sides of the mold exposed to air at room conditions (21-27° C.; 20-50% relative humidity) for a predetermined amount of time, normally 1 hr or 24 hrs. This predetermined amount of time begins at the time at which the aqueous solution comes into contact with the particulate composition at the beginning of the mixing process. Testing is performed on a mechanical test frame capable of displacement control and of monitoring displacement and force through data acquisition running at 20 Hz or faster. The sides of the specimen mold are removed immediately prior to testing; only the areas between the notches are removed.

Removal of the sides is normally performed with a knife. The top and bottom of the mold are held between two fingers with slight pressure to prevent specimen surface-to-mold interface damage. The knife blade is placed into one of the notches and then twisted to break the area between the notches free; this is repeated for the other side in the same manner. The tops and bottom of the molds are left in place to hold the specimen and prevent shear stresses on the surface. The specimen is placed between two flat, parallel platens; one of which is free to swivel to allow alignment with the loading train. The swiveling platen assures an equally distributed load across the specimen contact points. The specimen is loaded transversely at a rate of 5 mm/minute until failure. Proper failure will result in a vertical fracture completely through the length of the specimen. The maximum force at failure is noted.

A loading curve of force versus displacement is created to determine the maximum force at failure, in which displacement and force are positive values. The first part of the loading curve shows the loading of the foam followed by its compression. The compression of the foam portion will be evident by continued displacement with no substantial increase in force; this can also be seen visually during the test. After the foam is completely compressed, the force will begin to rise again, creating an increasing slope on the loading curve followed by a constant slope as the load is transferred to the specimen. The increasing slope is commonly known as a "toe in". Failure is defined as a sudden drop in load, a decrease in the slope of the loading curve after the constant slope from specimen loading has been established, and/or the force noted upon visual failure of the specimen while the test is running.

The diametral tensile strength in MPa is then calculated as followed: $(2*Pmax)/(\pi*L*H)$; where Pmax is the load at failure in Newtons, $\pi$ is approximately equal to 3.14, L is the length of the specimen in mm (25.4), and H is the height of the specimen in mm (16). Specimens are disqualified for diametral tensile strengths if any one or more of the following occur: fracture is not vertical, fracture does not completely run the length of the specimen, length of the specimen fails, or voids in the material are seen on the fractured walls of the specimen.

Dissolution Rates:

Dissolution rates for Inventive Composition A and the Comparative Composition are determined through the following methodology. Specimens are cast in silicone molds to a size of 4.8 mm outer diameter and 3.3 mm tall cylinders. A 3.3 mm thick sheet of silicone containing cylindrical voids is used as a mold. Cylindrical voids are 4.8 mm in outer diameter and 3.3 mm tall, and orientated such that the circular faces of the void are parallel and in the same plane as the surfaces of the silicone sheet.

A thin sheet of polyethylene is laid on a table. A polyethylene mesh is placed on top of the polyethylene sheet;

sheet and mesh are of same dimensions (excluding thickness) and positioned such that the mesh masks the sheet from the top. Next a silicone mold of smaller dimensions is placed on top of the mesh (excluding thickness). No part of the mold hangs off the edge of the mesh or sheet.

The material to be tested is then mixed together to form a homogeneous paste. The paste is then wiped across the top of the mold using a spatula in a manner that the voids are packed with the material. The mesh will allow air to be displaced out of the void as the mold is filled. Several wipes are performed to assure that material has completely penetrated to bottom of the mold and extruded out through the mesh and onto the lower polyethylene sheet. A final wipe with the spatula across the top of the mold is performed to remove the majority of excess material and produce smooth top faces for the specimens. Another polyethylene sheet of the same dimensions as the first is then placed across the top of the mold, such that it completely covers the top of the mold. This sheet is then gently pressed against the mold using a finger in a gentle rubbing motion. An intimate contact between the top polyethylene sheet and the specimens is created.

The entire system, sheet, mesh, mold, and sheet, is then picked up as a whole and flipped over in a manner such that the original top is now facing down. The system is held by hand and slapped repeatedly onto table in a manner such that any air entrapped in the molds will be displaced out by the material; slapping of the system should not be excessive in force or repetitions. Upon removal of the majority of the air the system is returned to table in the upside down orientation, sheet and mesh side up. The top polyethylene sheet, originally the bottom, and mesh are removed and the spatula is again used to wipe material into voids in the tops (previously bottoms) of the specimens created from air removal. A final wipe with the spatula across the top of the mold is performed to remove the majority of excess material. The sheet (no mesh) is returned to the top of the mold. The sheet is then pressed against the mold using a finger in a gentle rubbing motion. An intimate contact between the top and bottom polyethylene sheet and the specimens has now been created.

The specimens are left in the mold to cure for a minimum of 8 hrs after the second polyethylene sheet has been placed in direct contact with the specimens and mold (no mesh). After at least 8 hrs have passed, the specimens are demolded by hand. Any flash remaining attached to pellet faces are removed by rolling specimen between fingers. All defective specimens are disqualified from the test and discarded. A defective specimen is defined as a specimen not exhibiting a cylindrical shape, which could be caused by entrapped air, defects created upon demolding, and/or physical damage to the specimen itself.

All specimens which are not defective are spread across a stainless steel pan in a monolayer. The pan and specimens are then dried in an oven at 40° C. for a minimum of 4 hrs, and then removed from oven and allowed to cool for 30 minutes in room conditions (21-27° C.; 20-50% relative humidity).

From the specimens created, five (5) specimens are arbitrarily chosen to be used for dissolution testing. Each specimen chosen is paired with a clean cylindrical fitted glass extraction thimble of the following dimensions: 90.25 mm overall height, 4 mm fitted glass base (40-60 micron pores) located 80 mm from top of thimble, 25 mm outer diameter, and 22 mm inner diameter. The mass of each extraction thimble is measured (0.01 mg) and noted. The mass of each specimen in measured (0.01 mg) and noted. A polyethylene bottle (300 mL) is designated to each pair (specimen and thimble). The bottle has dimensions that allow thimble and specimen to easily be placed in and removed from bottle and upon filling with 275 mL of water will create a column of water that is taller than the thimble. The bottle is filled with 275 mL of distilled water at room temperature (21-27° C.). The specimen is placed into its corresponding thimble and the thimble is lowered into the bottle; care is taken to keep any part of the material from escaping from the thimble. The bottle is capped and placed into a water bath at 37° C. with no agitation and the time is noted.

At 24 hrs after the specimen has been in the water, the thimble containing the specimen is retrieved. The water is allowed to drain out of the thimble through the fitted glass base. The thimble containing the specimen is then dried for 4 hrs in a 40° C. oven or until completely dried (determined gravimetrically). The thimble containing the specimen is then allowed to cool down for 30 minutes at room conditions (21-27° C.; 20-50% relative humidity).

The thimble containing the pellet is then weighed to an accuracy of 0.01 mg. Subtracting the known empty thimble mass from the mass of the combination will result in the mass of the specimen alone. Subtracting this mass from the initial specimen mass will produce the mass lost to dissolution. This mass lost can be divided by the specimen initial mass and the product of that multiplied by 100 will result in the % mass lost from dissolution.

At this point the thimble containing the pellet is returned to the bottle containing fresh distilled water (275 mL) at room temperature (21-27° C.), and the bottle is capped and returned to the water bath. After 24 hrs the drying and weighing process is repeated. These actions are repeated with fresh distilled water after every 24 hr soak until the test is terminated or the material completely dissolves. The Inventive Composition A (indicated as "FastSet" in FIG. 3) provided a slightly slower daily accelerated dissolution than the Comparative Composition (indicated as "PD" in FIG. 3).

Example 2

A second exemplary embodiment of the presently disclosed composition is provided as follows, and was prepared specifically for the purposes of characterization and evaluation of the Inventive Composition against the Comparative Composition. It is noted that "Inventive Powder Composition A" as referenced in Table 6 is comparable to "Inventive Composition A" as referenced in Table 1; however, "Inventive Powder Composition A" as referenced in Table 6 does not include the MCPM and glycolic acid/saline solution of "Inventive Composition A." Table 7 indicates the relative mixing amounts of Inventive Powder Composition A, MCPM, and glycolic acid/saline solution to provide "Inventive Composition A."

TABLE 6

Inventive Powder Composition A

| Component | Percent by weight | Particle size range |
| --- | --- | --- |
| Calcium sulfate hemihydrate | 74.59% | 5 μm-10 μm |
| Accelerator (calcium sulfate) | 0.10% | ≤595 μm |
| Non-porous β-TCP granules | 10.37% | 180 μm-240 μm |
| Porous β-TCP granules (0-63 μm) | 2.59% | 0 μm-63 μm |
| Porous β-TCP granules (63-250 μm) | 7.78% | 63 μm-250 μm |
| Non-porous β-TCP powder | 4.57% | 13.3 μm-15.7 μm |

The components of Inventive Powder Composition A as shown in Table 6 were mixed. Inventive Powder Composition A, MCPM, and glycolic acid/saline solution were separately sterilized by gamma irradiation and combined in the amounts provided below in Table 7 for the tests indicated in the table.

TABLE 7

Inventive Composition A Makeup for Various Tests

| | Inventive Composition A | | |
|---|---|---|---|
| Test | Inventive Powder Composition A (g) | MCPM (g) | Glycolic Acid/Saline Solution (g) |
| FTIR | 19.28 | 0.72 | 5.00 |
| XRD | | | |
| Dissolution | | | |
| Maximum Exothermic Temperature | 24.10 | 0.90 | 6.25 |
| Vicat and Gillmore Set Time (wet) | 33.74 | 1.26 | 8.75 |
| Vicat and Gillmore Set Time (dry) | 33.74 | 1.26 | 8.75 |
| Dilute slurry pH | 24.10 | 0.90 | 6.25 |
| Density | 24.10 | 0.90 | 6.25 |
| Porosity | 24.10 | 0.90 | 6.25 |
| DTS (wet) | 57.85 | 2.15 | 15.00 |
| DTS (dry) | 57.85 | 2.15 | 15.00 |
| Injectability (Ejection) | 38.56 | 1.44 | 10.00 |

Chemical Composition (FTIR, XRD):

Inventive Powder Composition A, MCPM, and glycolic acid/saline solution were mixed and the resulting paste was spread onto a pellet mold and allowed to dry for a minimum of 8 hours at room temperature to give a pellet. The pellet was then oven dried at 40° C. for 5 hours and crushed to a powder using a mortar and pestle for analysis.

A ThermoScientific Nicolet i210g FTIR instrument was used for FTIR analysis using a diffuse reflectance method. The spectrum of Inventive Composition A exhibited peaks indicative of a calcium sulfate dihydrate, calcium sulfate hemihydrate, and tricalcium phosphate, correlating with the spectrum of the Comparative Composition.

A Rigaku MiniFlex X-Ray Diffraction instrument was used for XRD analysis. The Inventive Composition A demonstrated an almost full conversion from calcium sulfate hemihydrate form ($CaSO_4 \cdot \frac{1}{2} H_2O$) to the dihydrate form ($CaSO_4 \cdot 2H_2O$). Peaks of tricalcium phosphate ($Ca_3(PO_4)_2$) and brushite ($CaHPO_4 \cdot 2H_2O$) were also identified.

Physical Properties (pH, Maximum Exothermic Temperature, Dissolution, Porosity, and Density):

For pH determination, a loose slurry of the powder and liquid components of Inventive Composition A was mixed continuously for five minutes. At the end of the five minutes, pH was recorded. Three separate slurries were prepared and tested in this way, giving an average pH of 5.52 and a standard deviation of 0.02. The pH of Inventive Composition A was determined to be not significantly different than that of the Comparative Composition (p=0.074), based on a two-sample T-Test.

For maximum exothermic temperature determination, Inventive Powder Composition A and MCPM were mixed together, the glycolic acid/saline solution was added to the mixer, and the materials were mixed vigorously for 30 seconds under 22-25" vacuum to give Inventive Composition A. The paste was transferred to a polyethylene mold containing a thermocouple to record the temperature of the specimen. The temperature was recorded continuously as the material cured and the maximum was determined (based on ASTM F451). Three separate specimens were prepared and tested in this way, giving an average maximum exothermic temperature of 30.7 and a standard deviation of 0.1. The average maximum exothermic temperature of Inventive Composition A was determined to be significantly different than that of the Comparative Composition (p=0.000). A slight increase in reaction temperature is not unexpected due to the increased reaction rate for the Inventive Composition A and for all materials tested, the maximum temperature was advantageously well below the average body temperature of 37° C.

For dissolution testing, Inventive Powder Composition A and MCPM were mixed together, the glycolic acid/saline solution was added to the mixer, and the materials were mixed vigorously for 30 seconds under 22-25" vacuum to give Inventive Composition A. The resulting paste was spread onto a pellet mold and allowed to dry for a minimum of 8 hours at room temperature to give a pellet. The pellet was then oven dried at 40° C. for 5 hours. Changes in pellet weight were recorded after 96 hours of immersion in deionized water. Five trials were done and the average percentage of mass remaining in pellets comprising Inventive Composition A was 68.03%. The average dissolution of Inventive Composition A was determined to be not significantly different than that of the Comparative Composition (p=0.067), based on a Mann-Whitney test.

For porosity testing, Inventive Powder Composition A and MCPM were mixed together, the glycolic acid/saline solution was added to the mixer, and the materials were mixed vigorously for 30 seconds under 22-25" vacuum to give Inventive Composition A. The resulting paste was loaded into a 10 cc syringe and the syringe was tapped to remove air bubbles. The loaded syringe was air dried at room temperature, the end of the syringe was cut, and the sample was pushed out of the syringe. The resulting material was oven dried at 40° C. for 12 hours and broken in half by bending. The fracture surface was wet ground with alcohol to produce a smooth surface for analysis. The smoothed surface was examined with a microscope and porosity was evaluated by examination of the surface for visible pores at 7.5.times. The area of each void was measured using software and the total void area was calculated by summing the areas of all voids. The total void area of the section was divided by the total area of the fracture surface to determine percent porosity. The average percent porosity of Inventive Composition A was determined to be not significantly different than that of the Comparative Composition (p=1.00), based on a Mann-Whitney test.

For density testing, Inventive Powder Composition A and MCPM were mixed together, the glycolic acid/saline solution was added to the mixer, and the materials were mixed vigorously for 30 seconds under 22-25" vacuum to give Inventive Composition A. The resulting paste was loaded into a 15 cc open bore syringe and ejected into specimens approximately 1.5" long and 0.5" wide. The resulting specimen was dried at room temperature for 24 hours and then oven dried at 40° C. for 12 hours. After drying, the specimen was weighed and then submerged into a 10 cc graduated cylinder containing 5 mL deionized water and degassed in a sonicator for 3 minutes. The change in volume was measured visually on the graduated cylinder and the ratio was calculated by dividing the dried mass by the change in volume. The density of Inventive Composition A was determined to be not significantly different than that of the Comparative Composition (p=0.89), based on a two-sample t-test.

Performance Characteristics (Vicat Set Time, Gillmore Set Time, Injectability, and Diametral Tensile Strength):

For performance characteristic testing, Inventive Powder Composition A and MCPM were mixed together, the glycolic acid/saline solution was added to the mixer, and the materials were mixed vigorously for 30 seconds under 22-25" vacuum to give Inventive Composition A.

For Vicat set time determination, the paste was transferred to a small testing cup and evenly spread to create a material with constant thickness. A 300 g weight with an attached probe of 1 mm diameter was placed on the specimen and the specimen was considered to be "Vicat set" when the probe penetrated half the specimen thickness or less (as described in greater detail in Example 1). Vicat set time was determined in both "dry" (cured in air) and "wet" (cured in bovine serum) conditions. In both the dry and wet environments, Inventive Composition A had a significantly faster Vicat set time than the Comparative Composition (p=0.000 and p=0.005, respectively), based on a two-sample t-test.

The dry Vicat set time averages for specimens prepared from three different lots of Inventive Composition A (each lot used to prepare four specimens and the Vicat set times of these four specimens averaged to give a Lot Vicat set time average) were 12:38 (std. dev. 01:15), 10:38 (std. dev. 01:10), and 12:40 (std. dev. 01:26). The dry Vicat set time average for specimens prepared from the Comparative Composition (four specimens prepared and the Vicat set times of these four specimens averaged to give a Vicat set time average) was 16:50 (std. dev. 00:46).

The wet Vicat set time averages for specimens prepared from three different lots of Inventive Composition A (each lot used to prepare three specimens and the Vicat set times of these three specimens averaged to give a Lot Vicat set time average) were 13:40 (std. dev. 00:35), 11:40 (std. dev. 00:17), and 13:00 (std. dev. 00:17). The wet Vicat set time for the second lot of Inventive Composition A was significantly faster setting in the wet environment than the first and third lots (p=0.005, ANOVA); however, the difference in set times was not large and historically, wet testing has been more prone to variation within samples. The wet Vicat set time average for specimens prepared from the Comparative Composition (three specimens prepared and the Vicat set times of these three specimens averaged to give a Vicat set time average) was 18:15 (std. dev. 01:09).

For Gillmore set time determination, the paste was transferred to a small testing cup and evenly spread to create a material with constant thickness. The specimen was considered to be "Gillmore set" when the probe left no appreciable indentation on the surface of the specimen (as described in greater detail in Example 1). Gillmore set time was evaluated immediately after Vicat set time and was determined in both "dry" (cured in air) and "wet" (cured in bovine serum) conditions. In the dry environment, Inventive Composition A had a significantly faster Gillmore set time than the Comparative Composition (p=0.002), based on a two-sample t-test. In the wet environment, no data was available for the Comparative Composition and the Comparative Composition is typically not used under such conditions, so the Gillmore set time of Inventive Composition A in a wet environment could not be compared against that of the Comparative Composition.

The dry Gillmore set time averages for specimens prepared from three different lots of Inventive Composition A (each lot used to prepare four specimens and the Vicat set times of these four specimens averaged to give a Lot Gillmore set time average) were 16:08 (std. dev. 2:25), 13:00 (std. dev. 01:21), and 14:30 (std. dev. 02:05). The dry Vicat set time average for specimens prepared from the Comparative Composition (four specimens prepared and the Vicat set times of these four specimens averaged to give a Vicat set time average) was 47:00 (std. dev. 05:37).

The wet Vicat set time averages for specimens prepared from three different lots of Inventive Composition A (each lot used to prepare three specimens and the Vicat set times of these three specimens averaged to give a Lot Vicat set time average) were 17:50 (std. dev. 00:35), 15:20 (std. dev. 00:34), and 19:00 (std. dev. 01:30). The wet Vicat set time for the second lot of Inventive Composition A was significantly faster setting in the wet environment than the first and third lots (p=0.010, ANOVA); however, the difference in set times was not large and historically, wet testing has been more prone to variation within samples.

For injectability (ejection) determination, the paste was placed into a 20 cc syringe equipped with a 11 Ga, 6 cm Jamshidi needle. A force was applied to the syringe/needle system at the rate of 4.4 mm/sec until the specimen was ejected into a test cup. The resistance to ejection force at 15 mm displacement was recorded for the specimen at 3 minutes after initiation of mixing. The injectability of Inventive Composition A was determined to be not significantly different than that of the Comparative Composition (p=0.098), based on a two-sample t-test.

For diametral tensile strength, specimens were prepared and tested under dry conditions (as described in greater detail in Example 1). Specimens were also prepared and tested under wet conditions (i.e., a proteinaceous environment meant to simulate in situ conditions) by curing the paste for one hour, immersing the specimens in bovine serum, and heating the mixture at 37° C.+−1° C. A 2-hour test was performed by allowing the specimens to cure for one hour in bovine serum before testing and a 24-hour test was performed by allowing the specimens to cure for 23 hours in bovine serum. Specimens were then placed between the plates of a compression sub-press mounted in a test frame and compressed at a constant rate of 1.5 mm/min until fracture occurred.

The 2-hour diametral tensile strength of Inventive Composition A in both dry and wet conditions was determined to be significantly different (roughly a 20% increase in strength) than that of the Comparative Composition (p=0.001 for the dry conditions, based on a two-sample t-test and p=0.003 for the wet conditions, based on a Kruskal-Wallis test). A higher initial strength is consistent with the significantly faster set time of Inventive Composition A as compared with the Comparative Composition.

The 24-hour diametral tensile strength of Inventive Composition A in dry conditions was determined not to be significantly different than that of the Comparative Composition (p=0.061), based on a two-sample t-test. The 24-hour diametral tensile strength of Inventive Composition A in wet conditions was determined to be significantly different (with Inventive Composition A being stronger than the Comparative Composition) than that of the Comparative Composition (p=0.012), based on a two-sample t-test. The cause of this higher strength is not known, but the difference is relatively small (1.9 MPa) and likely due to known variation in data when materials are cured in a wet environment.

Overall, Inventive Composition A is statistically equivalent to the Comparative Composition both chemically and physically. Inventive Composition A provides improvements in performance characteristics by decreasing the Vicat and Gillmore set times while maintaining the strength and injectability of the material.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. A particulate composition adapted for forming a bone graft substitute cement upon mixing with an aqueous solution, comprising:
   i) a calcium sulfate hemihydrate powder, wherein the calcium sulfate hemihydrate is present at a concentration of at least about 50 weight percent based on the total weight of the particulate composition;
   ii) a monocalcium phosphate monohydrate powder;
   iii) a non-porous β-tricalcium phosphate powder; and
   iv) porous β-tricalcium phosphate particulates in the form of either a powder, granules, or a mixture of powder and granules, wherein the porous β-tricalcium phosphate particulates are present at a concentration of between about 5 and about 15 weight percent based on the total weight of the particulate composition.

2. The particulate composition of claim 1, wherein the calcium sulfate hemihydrate is present at a concentration of at least about 70 weight percent based on the total weight of the particulate composition.

3. The particulate composition of claim 1, wherein the calcium sulfate hemihydrate powder has a bimodal particle distribution.

4. The particulate composition of claim 3, wherein the calcium sulfate hemihydrate powder has a median particle size of about 5 to about 20 microns.

5. The particulate composition of claim 1, wherein the porous β-tricalcium phosphate particulates exhibits a bimodal particle size distribution.

6. The particulate composition of claim 5, wherein the porous β-tricalcium phosphate particulates comprises less than 50% by weight of particles having a particle size up to about 63 microns and greater than 50% by weight of particles having a particle size greater than about 63 microns.

7. The particulate composition of claim 5, wherein the porous β-tricalcium phosphate particulates comprises about 25% by weight of particles having a particle size up to about 63 microns and about 75% by weight of particles having a particle size greater than about 63 microns.

8. The particulate composition of claim 1, wherein the calcium sulfate hemihydrate is α-calcium sulfate hemihydrate.

9. The particulate composition of claim 1, wherein the calcium sulfate hemihydrate powder has a bimodal particle distribution comprising about 30 to about 60 volume percent of particles having a mode of about 1.0 to about 3.0 microns and about 40 to about 70 volume percent of particles having a mode of about 20 to about 30 microns, based on the total volume of the calcium sulfate hemihydrate powder.

10. The particulate composition of claim 1, further comprising an accelerant adapted for accelerating the conversion of calcium sulfate hemihydrate to calcium sulfate dihydrate.

11. The particulate composition of claim 10, wherein the accelerant is selected from the group consisting of calcium sulfate dihydrate particles, potassium sulfate particles, and sodium sulfate particles, wherein the accelerant is optionally coated with sucrose.

12. The particulate composition of claim 10, wherein the accelerant is present at a concentration of up to about 1 weight percent based on the total weight of the particulate composition.

13. The particulate composition of claim 1, wherein the porous β-tricalcium phosphate particulates have a pore size in the range from about 100 microns to about 400 microns.

14. The particulate composition of claim 1, wherein the porous β-tricalcium phosphate particulates is characterized by an interconnected, multidirectional porosity.

15. The particulate composition of claim 1, wherein the porous β-tricalcium phosphate particulates has a total porosity of at least about 50%.

16. The particulate composition of claim 1, further comprising a biologically active agent.

17. The particulate composition of claim 16, wherein the biologically active agent is selected from the group consisting of cancellous bone chips, growth factors, antibiotics, pesticides, chemotherapeutic agents, antivirals, analgesics, and anti-inflammatory agents.

18. The particulate composition of claim 16, wherein the biologically active agent is bone marrow aspirate.

19. The particulate composition of claim 16, wherein the biologically active agent is a growth factor selected from the group consisting of fibroblast growth factors, platelet-derived growth factors, bone morphogenic proteins, osteogenic proteins, transforming growth factors, LIM mineralization proteins, osteoid-inducing factors, angiogenins, endothelins; growth differentiation factors, ADMP-1, endothelins, hepatocyte growth factor and keratinocyte growth factor, heparin-binding growth factors, hedgehog proteins, interleukins, colony-stimulating factors, epithelial growth factors, insulin-like growth factors, cytokines, osteopontin, and osteonectin.

20. A particulate composition, comprising:
   i) a calcium sulfate hemihydrate powder having a bimodal particle distribution and a median particle size of about 5 to about 20 microns, wherein the calcium sulfate hemihydrate is present at a concentration of at least about 70 weight percent based on the total weight of the particulate composition;
   ii) a monocalcium phosphate monohydrate powder;
   iii) a non-porous β-tricalcium phosphate powder; and
   iv) porous β-tricalcium phosphate particulates, in an amount of between about 5 and about 15 weight percent based on the total weight of the particulate composition, wherein the porous β-tricalcium phosphate particulates comprises less than 50% by weight of particles having a particle size up to about 63 microns and greater than 50% by weight of particles having a particle size greater than about 63 microns.

21. The particulate composition of claim 20, wherein the porous β-tricalcium phosphate particulates have a pore size in the range from about 100 microns to about 400 microns.

22. The particulate composition of claim 20, wherein the porous β-tricalcium phosphate particulates is characterized by an interconnected, multidirectional porosity.

23. The particulate composition of claim 20, wherein the porous β-tricalcium phosphate particulates has a total porosity of at least about 50%.

24. The particulate composition of claim 1, wherein the non-porous β-tricalcium phosphate particulates is present at a concentration of between about 10 and about 15 weight percent based on the total weight of the particulate composition.

25. The particulate composition of claim 20, wherein the non-porous β-tricalcium phosphate particulates is present at a concentration of between about 10 and about 15 weight percent based on the total weight of the particulate composition.

* * * * *